United States Patent [19]
Patel et al.

[11] Patent Number: 5,599,920
[45] Date of Patent: Feb. 4, 1997

[54] PERIPHERAL MYELIN PROTEIN CODING SEQUENCE AND METHOD

[75] Inventors: Pragna I. Patel, Houston, Tex.; Ueli Suter, Menlo Park, Calif.; G. Jackson Snipes, Palo Alto, Calif.; Andrew Welcher, Newbury Park, Calif.; Marino DeLeon, Silver Springs, Md.; James R. Lupski, Houston, Tex.; Eric M. Shooter, Portola Valley, Calif.

[73] Assignee: Baylor College of Medicine, Houston, Tex.

[21] Appl. No.: 518,474

[22] Filed: Aug. 21, 1995

Related U.S. Application Data

[63] Continuation of Ser. No. 308,488, Sep. 19, 1994, abandoned, which is a continuation of Ser. No. 879,623, May 6, 1992, abandoned, which is a continuation-in-part of Ser. No. 711,615, Jun. 6, 1991.

[51] Int. Cl.$^6$ .................................................... C12N 15/12
[52] U.S. Cl. .................... 536/23.5; 435/172.3; 935/11
[58] Field of Search .................. 536/23.5; 435/320.1, 435/172.3

[56] References Cited

PUBLICATIONS

Kitamura et al (1976) Biochim. Biophys. Acta. 455 806–816.
Spreyer et al. (1991) EMBO. J. 10: 3661–3668.
Uyemura et al. (1978) Adv. Exp. Biol. Med. 100 95–115.
Snipes et al (1992) J. Cell Biol. 117: 225–238.
Manfioletti et al. (1990) Mol. Cell. Biol. 10: 2924–2934.
Welcher et al. (1991) Proc. Nat. Acad. Sci, USA, 88 7195–7199.

Primary Examiner—Robert A. Wax
Assistant Examiner—Gabriele E. Bugaisky
Attorney, Agent, or Firm—Fulbright & Jaworski L.L.P.

[57] ABSTRACT

The disclosed invention includes a a peripheral myelin protein, PMP-22, which is present predominantly in the peripheral nervous system and purified nucleic acids which encode the protein. Also included are oligonucleotide probes and primers derived from such sequences, and methods for the use of such sequences, probes and primers in detecting peripheral neuropathies.

1 Claim, 21 Drawing Sheets

```
A: 1▸ GCGCTCTCCTCGCAGGCAGAAACTCCGCTGAGCAGAACTTGCCGCCAGA ATG CTC CTC
B:                                                    1▸ Met Leu Leu

59  CTG TTG CTG AGT ATC ATC GTC CTC CAC GTC GCG GTG CTG GTG CTG CTG TTC
  4  Leu Leu Leu Ser Ile Ile Val Leu His Val Ala Val Leu Val Leu Leu Phe

110  GTC TCC ACG ATC GTC AGC CAA TGG ATC GTG GGC AAT GGA CAC GCA ACT GAT
 21  Val Ser Thr Ile Val Ser Gln Trp Ile Val Gly Asn Gly His Ala Thr Asp

161  CTC TGG CAG AAC TGT AGC ACC TCT TCC TCA GGA AAT GTC CAC CAC TGT TTC
 38  Leu Trp Gln Asn Cys Ser Thr Ser Ser Ser Gly Asn Val His His Cys Phe

212  TCA TCA TCA CCA AAC GAA TGG CTG CAG TCT GTC CAG GCC ACC ATG ATC CTG
 55  Ser Ser Ser Pro Asn Glu Trp Leu Gln Ser Val Gln Ala Thr Met Ile Leu

263  TCG ATC ATC TTC AGC ATT CTG TCT CTG TTC CTG TTC TTC TGC CAA CTC TTC
 72  Ser Ile Ile Phe Ser Ile Leu Ser Leu Phe Leu Phe Phe Cys Gln Leu Phe

314  ACC CTC ACC AAG GGG GGC AGG TTT TAC ATC ACT GGA ATC TTC CAA ATT CTT
 89  Thr Leu Thr Lys Gly Gly Arg Phe Tyr Ile Thr Gly Ile Phe Gln Ile Leu

365  GCT GGT CTG TGC GTG ATG AGT GCT GCG GCC ATC TAC ACG GTG AGG CAC CCG
106  Ala Gly Leu Cys Val Met Ser Ala Ala Ala Ile Tyr Thr Val Arg His Pro

416  GAG TGG CAT CTC ACC TCG GAT TAC TCC TAC GGT TTC GCC TAC ATC CTG GCC
123  Glu Trp His Leu Asn Ser Asp Tyr Ser Tyr Gly Phe Ala Tyr Ile Leu Ala

468  TGG GTG GCC TTC CCC CTG GCC CTT CTC AGC GGT GTC ATC TAT GTG ATC TTG
140  Trp Val Ala Phe Pro Leu Ala Leu Leu Ser Gly Val Ile Tyr Val Ile Leu

519  CGG AAA CGC GAA TGA GGCGCCCAGACGGTCTGTCTGAGGCTCTGAGCGTACATAGGG
157  Arg Lys Arg Glu ***

576  AAGGGAGGAAGGGAAAACAGAAAGCAGACAAAGAAAAAAGAGCTAGCCCAAAATCCCAAA
636  CTCAAACCAAACCAAACAGAAAGCAGTGGAGGTGGGGGTTGCTGTTGATTGAAGATGTAT
696  ATAATATCTCCGGTTTATAAAACCTATTTATAACACTTTTTACATATATGTACATAGTAT
756  TGTTTGCTTTTTATGTTGACCATCAGCCTCGTGTTGAGCCTTAAAGAAGTAGCTAAGGAA
816  CTTTACATCCTAACAGTATAATCCAGCTCAGTATTTTTGTTTTGTTTTTGTTTGTTTGT
876  TTTGTTTTACCCAGAAATAAGATAACTCCATCTCGCCCCTTCCCTTTCATCTGAAAGAAG
936  ATACCTCCCTCCCAGTCCACCTCATTTAGAAAACCAAAGTGTGGGTAGAAACCCCAAATG
996  TCCAAAAGCCCTTTTCTGGTGGGTGACCCAGTGCATCCAACAGAAACAGCCGCTGCCCGA
1056 ACCTCTGTGTGAAGCTTTACGCGCACACGGACAAAATGCCCAAACCGGAGCCCTCGAAAA
1116 ACGCGGCTTGTGGCATTGGCATACTTGCCTTACAGGTGGAGTATCTTCGTCACACATCTA
1176 AATGAGAAATCAGTGACAACAAGTCTTTGAAATGGTGCTATGGATTTACCATTCCTTATT
1236 ATCACTAATCATCTAAACAACTCACTGGAAATCCAATTAACAATTTTATAACATAAGATA
1296 GAATGGAGACCTGAATAATTCTGTGTAATATAAATGGTTTATAACTGCTTTTGTACCTAG
1356 CTAGGCTGCTATTATTACTATAATGAGTAAATCATAAAGCCTTCGTCACTCCCACAGTTT
1416 TCTTACGGTCGGAGCATCACAACAAGCGTCTAGACTCCTTGGGACCGTGAGTTCCTAGAG
1476 CTTGGCTGGGTCTAGGCTGTTCTGTGCCTCCAAGGACTGTCTGGCAATGACTTGTATTGG
1536 CCACCAACTGTAGATGTATATATGGTGCCCTTCTGATGCTAAGACTCCAGACCTTTTGTT
1596 TTTGCTTTGCATTTTCTGATTTATACCAACTGTGTGGACTAAGATGCATTAAAATAAACA
1656 TCAGAG 1661
```

```
                MLLLLLSIIVLHVAVLVLLFVSTIVSQWIVGNGHATDLWQNCSTSSSGNVHHCF
A. Human        ----------------------------------------------------
B, Rat          -----G-LF--I-------------L----R----T--AL-A-Q--Y
C. Mouse        -----G-LF--I-------------L----T----T--AL-A-Q--Y
D. Bovine       --------G----X-------------------------
```

TM 2                                    TM 3

```
            SSSPNEWLQSVQATMILSIIFSILSLFLFFCQLFTLTKGGRFYITGIFQILAGLC
Human       ----------------------------------------------------
Rat         ---VS-----------------V---V---------------V--------
Mouse       ---VS-------------V---V-A-----------------F--------
```

TM 4

```
            VMSAAAIYTVRHPEWHLNSDYSYGFAYILAWVAFPLALLSGVIYVILRKRE
Human       ----------------------------------------------------
Rat         ------------------S---V-N-------------I-----------
Mouse       ------------------S---V-T-------------I-----------
```

Figure 2

1   MLLLLLGILFLHIAVLVLLFVSTIVSQWLVGNGHTTDLWQ

41  NCTTSALGAVQHCYSSSVSEWLQSVQATMILSVIFSVLAL

81  FLFFCQLFTLTKGGRFYLTGFFQILAGLCVMSAAAIYTVR
                        ↓
121 HSEWHVNTDYSYGFAYILAWVAFPLALLSGIIYVILRKRE

Figure 13

```
   1 GGGGGAAGCCAGCAACCTAGAGGACGCCCCGAGTTTGTGCCTGAGGCTACTCCGCTCTGAGC
  64 CGGCTGTCCCTTTGAACTGAAAGCACCGCTCCACCGAGCCCGAGCCCAACTCCAGCCACCATG
                                                                   Met
 127 CTTCTACTCTTGTTGGGGATCCTGTTCCTTCACATCGCGGTGCTAGTGTTGCTCTTCGTCTCC
     LeuLeuLeuLeuLeuGlyIleLeuPheLeuHisIleAlaValLeuValLeuPheValSer
 190 ACCATCGTCAGCCAATGGCTCGTGGGCAATGGACACAGGACTGATCTCTGGCAGAACTGTACC
     ThrIleValSerGlnTrpLeuValGlyAsnGlyHisArgThrAspLeuTrpGlnAsnCysThr
 253 ACATCCGCCTTGGGAGCCGTCCAGCACTGCTACTCCTCATCTGTGAGCGAATGGCTTCAGTCT
     ThrSerAlaLeuGlyAlaValGlnHisCysTyrSerSerSerValSerGluTrpLeuGlnSer
 316 GTCCAGGCCACCATGATCCTGTCTGTCATCTTCAGCGTCCTGTCCCTGTTCCTGTTCTTCTGC
     ValGlnAlaThrMetIleLeuSerValIlePheSerValLeuSerLeuPheLeuPhePheCys
 379 CAGCTCTTCACTCTCACCAAGGCGGCCGCTTTTACATCACTGGAGTCTTCCAAATCCTTGCT
     GlnLeuPheThrLeuThrLysGlyGlyArgPheTyrIleThrGlyValPheGlnIleLeuAla
 442 GGTCTGTGTGTGATGAGTGCAGCGGCCATCTACACAGTGAGACACAGTGAGTGGCATGTCAAC
     GlyLeuCysValMetSerAlaAlaAlaIleTyrThrValArgHisSerGluTrpHisValAsn
 505 AACGACTACTCCTATGGCTTTGCTTACATCCTGGCCTGGGTGGCTTTCCCGCTGGCCCTCCTT
     AsnAspTyrSerTyrGlyPheAlaTyrIleLeuAlaTrpValAlaPheProLeuAlaLeuLeu
 568 AGTGGCATCATCTACGTGATCCTGCGGAAACGCGAATGAGGCGCCCGACGCACCATCCGTCTA
     SerGlyIleIleTyrValIleLeuArgLysArgGluEnd
 631 GGCTCTGAGCGTGCATAGGGTACACAGGGAGGGAGGAAGGAAACCAGAAAACCAAACCAACCA
 694 ACCCAAAAGAGCTAGCCCCCAAACCCAAACGCAAGCCAAACCAAACAGAACACAGTTGAGTGG
 757 GGATTGCTGTCGATTGAAGATGTATATAATATCTATGGTTTATAAAACCTATTTATAACACTT
 820 TTTACATACATGTACATAGGATTGTTTGCTTTTTATGTTGACCGTCAGCCTCGTGTTGAATCT
 883 TAAACGACTCTACATCCTAACACTATAACCAAGCTCAGTATTTTCGTTTTGTTTCGTTTTTTT
 946 CATCTTTTTGTTTTGCTCAGACATAAAAAAAAAAAAAAAATCCACGTGGCCCCCTTTCATCTG
1009 AAAGCAGATCCCTCCCTCCCATTCAACCTCATAGGATAACCAAAGTGCGGGGACAAACCCCAG
1072 ATGGCCAGAGGCCTTCACACTATGGGTGACCCAGTGAATTTAGCAGGAATAATCCGCTGCCCG
1135 AATCAATGTGTGAAGCCCTAAGCACTCACAGACGAAACGCCCTGACCAGAGCCCTCTGCGAAA
1198 CCAATAGCTGGTGGCTGCGGAACACTTGACCCTGAAGGCGGAGTACTGGGGCACATGTTTAAA
1261 TGAGACGTCAGAGACAAGCAATCTGTGAAATGGTGCTATAGATTTACCATTCCTTGTTATTAC
1324 TAATCATTTAAACCACTCACTGGAAACTCAATTAACAGTTTTATGACCTACAGCAGAACAGAG
1387 ACCCGATACAAACGGTTCGTAACTGCTTTCGTACATAGCTAGGCTGTTGTTATTACTACAATA
1450 AATAAATCTCAAAGCCTTCGTCACTCCCACAGTTTTCTCACGGTCGGAGCATCAGGACGAGGG
1513 TCTAGACCCTTGGGACTAGCAAATTCCCTGGCTTTCTGGGTCTAGAGTGTTCTGTGCCTCCAA
1576 GGACTGTCTAGCGATGACTTGTATTGGCCACCAACTGTAGATGTATATACGGTGTCCTTCTGA
1639 TGCTAAGACTCCAGACCTTTCTTGGTTTTGCTGGCTTTTTCTGATTTTATACCAACTGTGTGG
1702 ACTAAGATGCATTAAAATAAACATCAGAGTAACTC 1736
```

Figure 16A

```
  1 MLLLLLGILFLHIAVLVLLFVSTIVSQWLVGNGHRTDLWQ 40
    |||||||||||||||||||||||||||||||||| |||||
  1 MLLLLLGILFLHIAVLVLLFVSTIVSQWLVGNGHTTDLWQ 40

41 NCTTSALGAVQHCYSSSVSEWLQSVQATMILSVIFSVLSL 80
    |||||||||||||||||||||||||||||||||||| | 
 41 NCTTSALGAVQHCYSSSVSEWLQSVQATMILSVIFSVLAL 80

81 FLFFCQLFTLTKGGRFYITGVFQILAGLCVMSAAAIYTVR 120
    ||||||||||||||||||||| ||||||||||||||||||
 81 FLFFCQLFTLTKGGRFYITGFFQILAGLCVMSAAAIYTVR 120

121 HSEWHVNNDYSYGFAYILAWVAFPLALLSGIIYVILRKRE 160
    |||||||  |||||||    ::       :||
121 HSEWHVNTDYSYGFATSWPGWPFP                144
```

Figure 16B

```
         1                   17  40       44
SR-13    M L L L L G I L F L H I A V L V / Q N C T T
         | | | | | | | | : : | ! | | | |   | | | : |
PAS-II   M L L L L G I I V L X V A V L V / Q N C S T
         | | | | | | | | : : | ! | | | |   | | | : |
GAS-3    M L L L L G I L F L H I A V L V / Q N C T T
```

Figure 16C

A. $\overset{27}{Q}$ W L V G N G H R T D L W $\overset{42}{Q}$ N C - carboxyl

B. $\overset{117}{Y}$ T V R H S E W H V N N D $\overset{132}{Y}$ S Y - carboxyl

Figure 20

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1661 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| GCGCTCTCCT | CGCAGGCAGA | AACTCCGCTG | AGCAGAACTT | GCCGCCAGAA | TGCTCCTCCT | 60 |
| GTTGCTGAGT | ATCATCGTCC | TCCACGTCGC | GGTGCTGGTG | CTGCTGTTCG | TCTCCACGAT | 120 |
| CGTCAGCCAA | TGGATCGTGG | GCAATGGACA | CGCAACTGAT | CTCTGGCAGA | ACTGTAGCAC | 180 |
| CTCTTCCTCA | GGAAATGTCC | ACCACTGTTT | CTCATCATCA | CCAAACGAAT | GGCTGCAGTC | 240 |
| TGTCCAGGCC | ACCATGATCC | TGTCGATCAT | CTTCAGCATT | CTGTCTCTGT | TCCTGTTCTT | 300 |
| CTGCCAACTC | TTCACCCTCA | CCAAGGGGGG | CAGGTTTTAC | ATCACTGGAA | TCTTCCAAAT | 360 |
| TCTTGCTGGT | CTGTGCGTGA | TGAGTGCTGC | GGCCATCTAC | ACGGTGAGGC | ACCCGGAGTG | 420 |
| GCATCTCAAC | TCGGATTACT | CCTACGGTTT | CGCCTACATC | CTGGCCTGGG | TGGCCTTCCC | 480 |
| CCTGGCCCTT | CTCAGCGGTG | TCATCTATGT | GATCTTGCGG | AAACGCGAAT | GAGGCGCCCA | 540 |
| GACGGTCTGT | CTGAGGCTCT | GAGCGTACAT | AGGGAAGGGA | GGAAGGGAAA | ACAGAAAGCA | 600 |
| GACAAAGAAA | AAAGAGCTAG | CCCAAAATCC | CAAACTCAAA | CCAAACCAAA | CAGAAAGCAG | 660 |
| TGGAGGTGGG | GGTTGCTGTT | GATTGAAGAT | GTATATAATA | TCTCCGGTTT | ATAAAACCTA | 720 |
| TTTATAACAC | TTTTTACATA | TATGTACATA | GTATTGTTTG | CTTTTTATGT | TGACCATCAG | 780 |
| CCTCGTGTTG | AGCCTTAAAG | AAGTAGCTAA | GGAACTTTAC | ATCCTAACAG | TATAATCCAG | 840 |
| CTCAGTATTT | TTGTTTTGTT | TTTTGTTTGT | TTGTTTTGTT | TTACCCAGAA | ATAAGATAAC | 900 |
| TCCATCTCGC | CCCTTCCCTT | TCATCTGAAA | GAAGATACCT | CCCTCCCAGT | CCACCTCATT | 960 |
| TAGAAAACCA | AAGTGTGGGT | AGAAACCCCA | AATGTCCAAA | AGCCCTTTTC | TGGTGGGTGA | 1020 |
| CCCAGTGCAT | CCAACAGAAA | CAGCCGCTGC | CCGAACCTCT | GTGTGAAGCT | TTACGCGCAC | 1080 |

| | | | | | |
|---|---|---|---|---|---|
| ACGGACAAAA | TGCCCAAACC | GGAGCCCTCG | AAAAACGCGG | CTTGTGGCAT | TGGCATACTT | 1140 |
| GCCTTACAGG | TGGAGTATCT | TCGTCACACA | TCTAAATGAG | AAATCAGTGA | CAACAAGTCT | 1200 |
| TTGAAATGGT | GCTATGGATT | TACCATTCCT | TATTATCACT | AATCATCTAA | ACAACTCACT | 1260 |
| GGAAATCCAA | TTAACAATTT | TATAACATAA | GATAGAATGG | AGACCTGAAT | AATTCTGTGT | 1320 |
| AATATAAATG | GTTTATAACT | GCTTTTGTAC | CTAGCTAGGC | TGCTATTATT | ACTATAATGA | 1380 |
| GTAAATCATA | AAGCCTTCGT | CACTCCCACA | GTTTCTTAC | GGTCGGAGCA | TCACAACAAG | 1440 |
| CGTCTAGACT | CCTTGGGACC | GTGAGTTCCT | AGAGCTTGGC | TGGGTCTAGG | CTGTTCTGTG | 1500 |
| CCTCCAAGGA | CTGTCTGGCA | ATGACTTGTA | TTGGCCACCA | ACTGTAGATG | TATATATGGT | 1560 |
| GCCCTTCTGA | TGCTAAGACT | CCAGACCTTT | TGTTTTGCT | TTGCATTTTC | TGATTTTATA | 1620 |
| CCAACTGTGT | GGACTAAGAT | GCATTAAAAT | AAACATCAGA | G | | 1661 |

(2) INFORMATION FOR SEQ ID NO:2:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:2:

```
Met Leu Leu Leu Leu Leu Ser Ile Ile Val Leu His Val Ala Val Leu
 1               5                  10                  15
Val Leu Leu Phe Val Ser Thr Ile Val Ser Gln Trp Ile Val Gly Asn
                20                  25                  30
Gly His Ala Thr Asp Leu Trp Gln Asn Cys Ser Thr Ser Ser Ser Gly
            35                  40                  45
Asn Val His His Cys Phe
        50
```

(2) INFORMATION FOR SEQ ID NO:3:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:3:

```
Met Leu Leu Leu Leu Leu Gly Ile Leu Phe Leu His Ile Ala Val Leu
 1               5                  10                  15
Val Leu Leu Phe Val Ser Thr Ile Val Ser Gln Trp Leu Val Gly Asn
                20                  25                  30
Gly His Arg Thr Asp Leu Trp Gln Asn Cys Thr Thr Ser Ala Leu Gly
            35                  40                  45
Ala Val Gln His Cys Tyr
        50
```

(2) INFORMATION FOR SEQ ID NO:4:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: cDNA ( x i ) SEQUENCE DESCRIPTION: SEQ ID NO:4:

Met Leu Leu Leu Leu Leu Gly Ile Leu Phe Leu His Ile Ala Val Leu
1               5                   10                  15

Val Leu Leu Phe Val Ser Thr Ile Val Ser Gln Trp Leu Val Gly Asn
            20                  25                  30

Gly His Thr Thr Asp Leu Trp Gln Asn Cys Thr Thr Ser Ala Leu Gly
        35                  40                  45

Ala Val Gln His Cys Tyr
        50

( 2 ) INFORMATION FOR SEQ ID NO:5:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Met Leu Leu Leu Leu Leu Gly Ile Ile Val Leu Xaa Val Ala Val Leu Val
1               5                   10                  15

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Gln Asn Cys Ser Thr
1               5

( 2 ) INFORMATION FOR SEQ ID NO:7:

( i ) SEQUENCE CHARACTERISTICS:
        ( A ) LENGTH: 1736 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
GGGGGAAGCC  AGCAACCTAG  AGGACGCCCC  CGAGTTTGTG  CCTGAGGCTA  CTCCGCTCTG     60
AGCCGGCTGT  CCCTTTGAAC  TGAAAGCACC  GCTCCACCGA  GCCCGAGCCC  AACTCCAGCC    120
ACCATGCTTC  TACTCTTGTT  GGGGATCCTG  TTCCTTCACA  TCGCGGTGCT  AGTGTTGCTC    180
TTCGTCTCCA  CCATCGTCAG  CCAATGGCTC  GTGGGCAATG  GACACAGGAC  TGATCTCTGG    240
CAGAACTGTA  CCACATCCGC  CTTGGGAGCC  GTCCAGCACT  GCTACTCCTC  ATCTGTGAGC    300
GAATGGCTTC  AGTCTGTCCA  GGCCACCATG  ATCCTGTCTG  TCATCTTCAG  CGTCCTGTCC    360
CTGTTCCTGT  TCTTCTGCCA  GCTCTTCACT  CTCACCAAAG  GCGGCCGCTT  TTACATCACT    420
GGAGTCTTCC  AAATCCTTGC  TGGTCTGTGT  GTGATGAGTG  CAGCGGCCAT  CTACACAGTG    480
AGACACAGTG  AGTGGCATGT  CAACAACGAC  TACTCCTATG  CTTTGCTTA   CATCCTGGCC    540
TGGGTGGCTT  TCCCGCTGGC  CCTCCTTAGT  GGCATCATCT  ACGTGATCCT  GCGGAAACGC    600
```

| | | | | | |
|---|---|---|---|---|---|
| GAATGAGGCG | CCCGACGCAC | CATCCGTCTA | GGCTCTGAGC | GTGCATAGGG | TACACAGGGA | 660 |
| GGGAGGAAGG | AAACCAGAAA | ACCAAACCAA | CCAACCCAAA | AGAGCTAGCC | CCCAAACCCA | 720 |
| AACGCAAGCC | AAACCAAACA | GAACACAGTT | GAGTGGGGAT | GCTGTCGAT | TGAAGATGTA | 780 |
| TATAATATCT | ATGGTTTATA | AAACCTATTT | ATAACACTTT | TTACATACAT | GTACATAGGA | 840 |
| TTGTTTGCTT | TTTATGTTGA | CCGTCAGCCT | CGTGTTGAAT | CTTAAACGAC | TCTACATCCT | 900 |
| AACACTATAA | CCAAGCTCAG | TATTTTCGTT | TTGTTTCGTT | TTTTCATCT | TTTTGTTTTG | 960 |
| CTCAGACATA | AAAAAAAAAA | AAAATCCAC | GTGGCCCCCT | TTCATCTGAA | AGCAGATCCC | 1020 |
| TCCCTCCCAT | TCAACCTCAT | AGGATAACCA | AAGTGCGGGG | ACAAACCCCA | GATGGCCAGA | 1080 |
| GGCCTTCACA | CTATGGGTGA | CCCAGTGAAT | TTAGCAGGAA | TAATCCGCTG | CCCGAATCAA | 1140 |
| TGTGTGAAGC | CCTAAGCACT | CACAGACGAA | ACGCCCTGAC | CAGAGCCCTC | TGCGAAACCA | 1200 |
| ATAGCTGGTG | GCTGCGGAAC | ACTTGACCCT | GAAGGCGGAG | TACTGGGGCA | CATGTTTAAA | 1260 |
| TGAGACGTCA | GAGACAAGCA | ATCTGTGAAA | TGGTGCTATA | GATTTACCAT | TCCTTGTTAT | 1320 |
| TACTAATCAT | TTAAACCACT | CACTGGAAAC | TCAATTAACA | GTTTATGAC | CTACAGCAGA | 1380 |
| ACAGAGACCC | GATACAAACG | GTTCGTAACT | GCTTTCGTAC | ATAGCTAGGC | TGTTGTTATT | 1440 |
| ACTACAATAA | ATAAATCTCA | AAGCCTTCGT | CACTCCCACA | GTTTTCTCAC | GGTCGGAGCA | 1500 |
| TCAGGACGAG | GGTCTAGACC | CTTGGGACTA | GCAAATTCCC | TGGCTTTCTG | GGTCTAGAGT | 1560 |
| GTTCTGTGCC | TCCAAGGACT | GTCTAGCGAT | GACTTGTATT | GGCCACCAAC | TGTAGATGTA | 1620 |
| TATACGGTGT | CCTTCTGATG | CTAAGACTCC | AGACCTTTCT | TGGTTTTGCT | GGCTTTTTCT | 1680 |
| GATTTTATAC | CAACTGTGTG | GACTAAGATG | CATTAAAATA | AACATCAGAG | TAACTC | 1736 |

( 2 ) INFORMATION FOR SEQ ID NO:8:

( i ) SEQUENCE CHARACTERISTICS:
( A ) LENGTH: 144 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

| Met | Leu | Leu | Leu | Leu | Leu | Gly | Ile | Leu | Phe | Leu | His | Ile | Ala | Val | Leu |
|---|---|---|---|---|---|---|---|---|---|---|---|---|---|---|---|
| 1 | | | | 5 | | | | | 10 | | | | | 15 | |
| Val | Leu | Leu | Phe | Val | Ser | Thr | Ile | Val | Ser | Gln | Trp | Leu | Val | Gly | Asn |
| | | | 20 | | | | | 25 | | | | | 30 | | |
| Gly | His | Thr | Thr | Asp | Leu | Trp | Gln | Asn | Cys | Thr | Thr | Ser | Ala | Leu | Gly |
| | | 35 | | | | | 40 | | | | | 45 | | | |
| Ala | Val | Gln | His | Cys | Tyr | Ser | Ser | Val | Ser | Glu | Trp | Leu | Gln | Ser | |
| | 50 | | | | | 55 | | | | | 60 | | | | |
| Val | Gln | Ala | Thr | Met | Ile | Leu | Ser | Val | Ile | Phe | Ser | Val | Leu | Ala | Leu |
| 65 | | | | | 70 | | | | | 75 | | | | | 80 |
| Phe | Leu | Phe | Phe | Cys | Gln | Leu | Phe | Thr | Leu | Thr | Lys | Gly | Gly | Arg | Phe |
| | | | | 85 | | | | | 90 | | | | | 95 | |
| Tyr | Ile | Thr | Gly | Phe | Phe | Gln | Ile | Leu | Ala | Gly | Leu | Cys | Val | Met | Ser |
| | | | 100 | | | | | 105 | | | | | 110 | | |
| Ala | Ala | Ala | Ile | Tyr | Thr | Val | Arg | His | Ser | Glu | Trp | His | Val | Asn | Thr |
| | | | 115 | | | | | 120 | | | | | 125 | | |
| Asp | Tyr | Ser | Tyr | Gly | Phe | Ala | Thr | Ser | Trp | Pro | Gly | Trp | Pro | Phe | Pro |
| | | | 130 | | | | 135 | | | | | 140 | | | |

( 2 ) INFORMATION FOR SEQ ID NO:9:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:9:

Met Leu Leu Leu Leu Leu Gly Ile Leu Phe Leu His Ile Ala Val Leu Val
1               5                   10                  15

( 2 ) INFORMATION FOR SEQ ID NO:10:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

Met Leu Leu Leu Leu Leu Gly Ile Ile Val Leu Xaa Val Ala Val Leu Val
1               5                   10                  15

( 2 ) INFORMATION FOR SEQ ID NO:11:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:11:

Met Leu Leu Leu Leu Leu Gly Ile Leu Phe Leu His Ile Ala Val Leu Val
1               5                   10                  15

( 2 ) INFORMATION FOR SEQ ID NO:12:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:12:

Gln Asn Cys Thr Thr
1               5

( 2 ) INFORMATION FOR SEQ ID NO:13:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:13:

Gln Trp Leu Val Gly Asn Gly His Arg Thr Asp Leu Trp Gln Asn Cys
1               5                   10                  15

( 2 ) INFORMATION FOR SEQ ID NO:14:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:14:

```
Tyr  Thr  Val  Arg  His  Ser  Glu  Trp  His  Val  Asn  Asn  Asp  Tyr  Ser  Tyr
1                   5                        10                       15
```

PERIPHERAL MYELIN PROTEIN CODING SEQUENCE AND METHOD

This application is a continuation of application Ser. No. 08/308,488, filed Sep. 19, 1994, now abandoned which is a continuation of application Ser. No. 07/879,623, filed May 6, 1992, now abandoned which is a Continuation-in-Part of U.S. patent application Ser. No. 07/711,615, filed Jun. 6, 1991.

FIELD OF THE INVENTION

The present invention relates to nucleic acid coding sequences, nucleic acid probes, deduced amino acid sequences and antibodies directed thereto for human peripheral myelin protein PMP-22 and to methods for using such sequences in the detection and diagnosis of CMT1A in human subjects.

REFERENCES

1. Charcot, J.-M. & Marie, P. Sur une forme particulaiere d'atrophie musculaire progressive souvent familiale debutant par les pied et les jambes et atteignant plus tard les mains. Rev. Med. 6, 97–138 (1886).

2. Lupski, J. R., et al., Charcot-Marie-Tooth Syndrome: Clinical Electrophysiological and Genetic Aspects. In: Current Neurology. Appel S, ed. Chicago: Mosby-Yearbook, 1–25, (1991).

3. Lupski, J. R., et al: DNA duplication associated with Charcot-Marie-Tooth disease type 1A. Cell 66, 219–232 (1991).

4. Skre, H. Genetic and clinical aspects of Charcot-Marie-Tooth's disease. Clin. Genet. 6, 98–118 (1974).

5. Lupski, J. R., et al: Gene dosage effect is a mechanism for Charcot-Marie-Tooth disease type 1A. Nature Genet. 1, 29–33 (1992).

6. Raeymaekers, P., et al: Duplication in chromosome 17p11.2 in Charcot-Marie-Tooth neuropathy type 1A (CMT 1A). Neuromuscular Disorders 1, 93–97 (1991).

7. Raeymaekers, P., et al., Estimation of the size of the chromosome 17p11.2 duplication Charcot-Marie-Tooth neuropathy type 1a (CMT1a).J. Med. Genet. 29, 5–11 (1992).

8. Hoogendijk J. E., et al. The duplication in Charcot-MarieTooth disease type 1a spans at least 1100 kb on chromosome 17p11.2. Hum. Genet. 88, 215–218 (1991).

9. Falconer, D. S. Two new mutants, "trembler" and "reeler," with neurological action in the house mouse (Mus musculus L. J. Genet. 50, 192–201 (1951).

10. Henry, E. W., et al., Comparison of Trembler and Trembler-J mouse phenotypes: varying severity of peripheral hypomyelination. J. Neuropathol. Exp. Neurol. 42, 688 (1983).

11. Davisson M. T. & Roderick, T. H. Cytogenet. Cell Genet. 22, 552–564 (1977).

12. Buchberg, A. M., et al., A comprehensive genetic map of murine chromosome 11 reveals extensive linkage conservation between mouse and human. Genetics 122, 153–161 (1989).

13. Buchberg, A. M., et al., Mouse chromosome 11. Mammal. Genome 1, 5158–5191 (1991).

14. Suter, U., et al. The Trembler mouse carries a point mutation in a myelin gene. Nature 356, 241–244 (1992).

15. Suter, U., et al. A leucine-to-proline mutation in the putative first transmembrane domain of the 22-kDa peripheral myelin protein in the trembler-J mouse. Proc. Natl. Acad. Sci. USA, in press.

16. Snipes, G. J., et al., Characterization of a novel peripheral nervous system myelin protein (PMP-22/SR13). J. Cell Biol. 117, 225–238 (1992).

17. Henry, E. W. & Sidman, R. L. Long lives for homozygous Trembler mutant mice despite virtual absence of peripheral nerve myelin. Science 241, 344–346 (1988).

18. Perkins, C. S., et al. Schwann cell multiplication in trembler mice. Neuropathol. App. Neurobiol. 7, 115–126 (1981).

19. Kitamura, K., et al. Microheterogeneity of carbohydrate in PO protein from bovine peripheral nerve myelin. In: Proceedings of the 6th International Symposium on Glycoconjugates. Yamaka T., et al., eds. Tokyo: Japan Scientific Societies Press, 273–274 (1981).

20. Manfoletti, G., et al., A growth arrest-specific (gas) gene codes for a membrane protein. Mol. Cell Biol. 10 2924–2930 (1990).

21. Welcher, A. A., et al. A myelin protein is encoded by the homologue of a growth arrest-specific gene. Proc. Natl. Acad. Sci. USA 88, 7195–7199 (1991).

22. Guzzetta V., et al.: Somatic cell hybrids, sequence tagged sites, simple repeat polymorphisms and yeast artificial chromosomes for physical and genetic mapping of proximal 17p. Genomics, in press (1992).

23. Low, P.A. The evolution of 'onion bulbs' in the hereditary hypertrophic neuropathy of the Trembler mouse. Neuropathol. App. Neurobiol. 3, 81–92 (1977).

24. Low, P. A., & McLeod, J. G. Hereditary demyelinating neuropathy in the Trembler mouse. J. Neurol. Sci. 26, 565–574 (1975).

25. Low, P. A. Hereditary hypertrophic neuropathy in the Trembler mouse. Part 1. J. Neurol. Sci. 30, 327–341 (1976).

26. Low, P.A. Hereditary hypertrophic neuropathy in the Trembler mouse. Part 2. J. Neurol. Sci. 30, 343–368 (1976).

27. Dyck, P. J. Inherited neuronal degeneration and atrophy affecting peripheral motor, sensory, and autonomic neurons in Dyck. In: Peripheral Neuropathy. Thomas et al., eds. Philadelphia: WB Saunders Company, 1600–1655 (1984).

28. Aguayo, et al. Abnormal myelination in transplanted Trembler mouse Schwann cells. Nature 265, 73 (1977).

29. Nukada, H., et al., Thin axons relative to myelin spiral length in hereditary motor and sensory neuropathy, type 1. Ann. Neurol. 14, 648–655 (1983).

30. Nukada, H., & Dyck, P. J., Decreased axon caliber and neurofilaments in hereditary motor and sensory neuropathy, type 1. Ann. Neurol. 16, 238–241 (1984).

31. de Waegh, S. M., et al., Local modulation of neurofilament phosphorylation, axonal caliber, and slow axonal transport by myelinating Schwann cells. Cell 68, 451–463 (1992).

32. De Leon, et al., Identification of transcriptionally regulated genes after sciatic nerve injury. J. Neurosci. Res. 26, 437–448 (1991).

33. Spreyer, P., et al. Axon-regulated expression of a Schwann cell transcript that is homologous to a 'growth arrest-specific' gene. EMBO J. 10, 3661–3668 (1991).

34. Morgan, L., et al., The effects of cAMP on differentiation of cultured Schwann cells: Progression from an early phenotype to a myelin phenotype depends on growth inhibition. J. Cell Biol. 112, 457–467 (1991).

35. Francke, U., et al., Chromosomal mapping of genes involved in growth control. CSH Symp. Quant. Biol. 20, 855–856 (1986).

36. Francke, U., & Busby, N., Assignments of the human genes for lactate dehydrogenase-A and thymidine kinase to specific chromosomal regions. Cytogenet. Cell Genet. 14, 313–319 (1975).

37. vanTuinen, P, et al., Regional mapping panel for human chromosome 17: application to neurofibromatosis type 1. Genomics 1, 374–381 (1987).

38. Greenberg, F., et al: Molecular analysis of the Smith-Magenis syndrome: a possible contiguous gene syndrome associated with del(17)(p11.2). Am. J. Hum. Genet. 49, 1207–1218 (1991).

39. Elder, F. F. B., et al., Unbalanced translocation (15;17) (q13:p13.3) with apparent Prader-Willi syndrome but without Miller-Dicker syndrome. Am. J. Med. Genet. 20, 519–524 (1985).

40. Chirgwin, J. M., et al., Isolation of biologically active ribonucleic acid from sources enriched in ribonuclease. Biochem. 18, 5294–5299 (1979).

41. Chomczynski, P., & Sacchi, N. Single-step method of RNA isolation by acid guanidinium thiocyanate-phenol-chloroform extraction. Anal. Biochem. 162, 156–159 (1987).

42. Fuqua, S. A. W., et al., A simple polymerase chain reaction method for detection and cloning of low-abundance transcripts. BioTechniques 9, 206–210 (1990).

43. Evans, G. A., et al., High efficiency vectors for cosmid microcloning and genomic analysis. Gene 79, 9–20 (1989).

44. Patel, P. I., et al., Isolation of a marker linked to the Charcot-Marie-Tooth disease type 1A gene by differential Alu-PCR of human chromosome 17-retaining hybrids. Am. J. Hum. Genet. 47, 926–934 (1990).

45. Wright, E. C., et al., A genetic map of human chromosome 17p. Genomics 7, 103–109 (1990).

46. Trask, B. J., et al., Mapping of human chromosome Xq28 by two-color fluorescence in situ hybridization of DNA sequences to interphase cell nuclei. Am. J. Hum. Genet. 48:1–15 (1991).

47. Falconer, D. S., J. Genetics 50:192–201 (1951)

48. Davisson, M. T., and Roderick, T. H., Cytogenet. Cell Genet. 22:552–564 (1978)

49. Aguayo, A. J., et al., Nature 265:73–75 (1977)

50. Henry, E. W., and Sidman, R. L., Science 241:344–346 (1988)

51. Henry, E. W., et al., J. Neuropathol. Exp. Neurol. 42:688–706 (1983)

52. Perkins, C. S., et al., Neuropathol. Appl. Neurobiol. 7:115–126 (1981)

53. De Leon, M., et al., J. Neurosci. Res. 26:437–448 (1991)

54. Welcher, A. A., et al., Proc. Natl. Acad. Sci. USA 88:7195–7199 (1991)

55. Lupski, J. R., et al., Cell 66:219–232 (1991)

56. Dyck, P. J., et al., Mayo Clin. Proc. 46:432–436 (1971)

57. Manfioletti, G., et al., Mol. Cell. Biol. 10:2924–2930 (1990)

58. Pham-Dinh, D., et al., Proc. Natl. Acad. Sci. USA 88:7562–7566 (1991)

59. Munke, M., et al., Cytogenet. Cell. Genet. 42:236–240 (1986)

60. McAlpine, P. J., et al., Genomics 7:408–415 (1990)

61. Munke, M., and Francke, U., J. Mol. Evol. 25:134–140 (1987)

62. Devereux, J., et al., Nucleic Acids Res. 12:387–392 (1984)

63. Trapp, B. D., et al., (1988) *J. Neurosci* 8:3515–3521.

64. LeBlanc, A. C., et al. (1987) *Mol Brain Res* 2:56–67.

65. von Heijne, G. (1986) *Nucleic Acids Res* 14:4683–4690.

66. Bilofsky, J. S. et al. (1986) *Nucleic Acids Res* 14:1–4.

67. Schneider, C. et al. (1988) Cell 54:787–793.

68. Manfioletti, G. et al. (1990) *Mol Cell Biol* 10:2924–2930.

69. Kitamura, K. et al. (1976) *Biochim Biophys Acta* 455:806–816.

70. Kitamura, K. et al. (1981) in Proceedings of the *6th International Symposium on Glycoconjugates*, eds. Yamaka, T., et al., (Jpn. Sci. Soc. Press, Tokyo), pp. 273–274.

71. Uyemura, K. et al. (1979) *J. Neurochem* 32:779–788.

72. Chomcyznski, P., et al. (1987) *Anal Biochem* 162:156–159.

73. DeLeon, M., et al. (1991) *J Neurosci Res, in press.*

74. Sanger, F., et al. (1977) PNAS USA 74:5463–5467.

75. Devereux, J., et al. (1984) *Nucleic Acids Res* 12:387–392.

76. Seed, B. (1987) *Nature* (London) 329:840–842.

77. Welcher, A., et al. (1991) *PNAS USA* 88:159–163.

78. Sternberger, L. D., ed., (1974) *Immunocytochemistry* (Prentice-Hall, Englewood Cliffs, N.J.).

79. Crea, R., U.S. Pat. No. 4,888,286, issued Dec. 19, 1989.

80. Eaton, M. A. W., et al., U.S. Pat. No. 4,719,180, issued Jan. 12, 1988.

81. Yoshio, T., et al., U.S. Pat. No. 4,849,350, issued Jul. 18, 1989.

82. Mullis, K. B., et al., U.S. Pat. No. 4,683,195, issued 28 Jul. 1987.

83. Mullis, K., U.S. Pat. No. 4,683,202, issued Jul. 28, 1987.

84. Maniatis, T., et al. *Molecular Cloning: A Laboratory Manual*, Cold Spring Harbor Laboratory (1982).

85. Ausubel, F. M., et al., Current Protocols in Molecular Biology, John Wiley and Sons, Inc., Media, Pa.

86. Harlow, E., et al., *Antibodies: A Laboratory Manual*, Cold Spring Harbor Press, Cold Spring Harbor, N.Y. (1988).

BACKGROUND OF THE INVENTION

Parent U.S. application Ser. No. 07/711,615, which is herein incorporated by reference, describes methods for detecting CMT1A disease in those persons having DNA duplication of a gene locus, such as the locus located on chromosome 17, using as probes, cosmid vectors directed to the VAW409 gene locus. CMT1A characterized by gene duplication is estimated to account for about 80% of all cases of CMT1A disease. The remaining 20% of CMT1A afflicted persons are thought to have another type of abnormality of this gene. In a mouse model of peripheral neuropathy, it has been shown that point mutations of the PMP-22 sequence are associated with Schwann cell defects characterized by severe hypomyelination and continuing Schwann cell proliferation throughout life (Suter et al.

1992). Such defects are also observed seen in human hypertrophic neuropathies, including CMT and Dejerine-Sottas disease, and it is now thought that mutations of the PMP-22 coding region may account for such defects.

In the present application is described the nucleic acid sequence for the specific peripheral myelin protein known as PMP-22. Information derived from this sequence is useful in the manufacture of a reagents useful in the diagnosis and therapy of human hypertrophic neuropathies, and particularlly, CMT type 1A.

SUMMARY OF THE INVENTION

In one embodiment, the invention includes a purified nucleic acid sequence which encodes a peripheral myelin protein protein. The peripheral myelin protein is characterized by (i) expression predominantly by peripheral Schwann cells, (ii) a molecular weight of about 20,000, and (iii) substantial sequence homology to a peripheral myelin protein obtained from human peripheral nervous tissue. In a preferred embodiment the nucleic acid sequence is a nucleic acid sequence which encodes a protein sequence selected from the group: SEQ ID NO: 2, SEQ ID NO: 3, and SEQ ID NO: 4. In yet another preferred embodiment, the nucleic acid sequence is SEQ ID NO: 1.

In another embodiment, the invention includes a human peripheral myelin protein. This protein is characterized by i) expression by peripheral Schwann cells, ii) a molecular weight of about 20,000, and iii) substantial sequence homology to a peripheral myelin protein obtained from human peripheral nervous tissue. In a preferred embodiment, the protein has an amino acid sequence selected from the group: SEQ ID NO: 2, SEQ ID NO: 3 and SEQ ID NO: 4.

The invention also includes a method for the detection of nucleic acid sequences homologous to human peripheral myelin protein (PMP-22) in a polynucleotide sample. The method includes the use of oligonucleotide probes derived from DNA sequences which encode a polypeptide from the group SEQ ID NO: 2, SEQ ID NO: 3, and SEQ ID NO: 4. In a preferred embodiment, the DNA sequence used to generate probes is SEQ ID NO: 1. The oligonucleotides are hybridized to the polynucleotide sample. The method also includes means for detecting the binding of the probes to sample polynucleotides.

The invention also includes, other embodiments, oligonucleotide probes and primers derived from DNA sequences which encode the polypeptide whose sequence is selected from the group: SEQ ID NO: 2, SEQ ID NO: 3, and SEQ ID NO: 4. In a preferred embodiment the oligonucleotide probe is derived from the DNA sequence: SEQ ID NO: 1. Primers of the invention are, in one embodiment, wherein the oligonucleotide sequences are derived from DNA sequences complementary to the DNA sequences described above.

In a further embodiment, the invention includes a method for isolating a target nucleic acid sequence homologous to nucleic acid sequences encoding PMP-22. The method includes selecting first and second oligonucleotide primers wherein the first oligonucleotide primer sequence is derived from DNA sequences which encode the polypeptides of the group: SEQ ID NO:2, SEQ ID NO:3, and SEQ ID NO:4. The second oligonucleotide primer sequence is derived from DNA sequences complementary to these DNA sequences. The method includes preparation of an amplification mixture containing the sample polynucleotide, the two primers, all four deoxynucleoside triphosphates, and a DNA polymerase, and reacting the mixture until desired degree of amplification of the target sequence has been achieved. The amplified target sequences are isolated.

BRIEF DESCRIPTION OF THE FIGURES

FIG. 1A shows the nucleotide sequence of a human PMP-22 cDNA (SEQ ID NO: 1);

FIG. 1B shows the predicted amino acid sequence of a human PMP-22 protein (SEQ ID NO: 2);

FIGS. 2A–2D show a comparison of deduced PMP-22 amino acid sequences derived from cloned cDNA sequences of human (FIG. 2A, SEQ ID NO: 2), rat (FIG. 2B, SEQ ID NO: 3), and mouse (FIG. 2C, SEQ ID NO: 4) and from direct amino acid sequencing from two regions of the bovine PASII protein (FIG. 2D, SEQ ID NO: 5 and SEQ ID NO: 6), where amino acid residues differing from the human sequence are indicated by single amino acid letter code, X indicates an undetermined residue, amino acid residues which are identical to the human sequence are indicated by hyphens, and TM indicates putative transmembrane regions;

FIG. 10A) and a Trembler (+/Tr; FIG. 10B) littermate mouse stained with alkaline toluidine blue;

FIG. 13 shows the deduced amino acid sequence of the mouse PMP-22 protein (SEQ ID NO: 4);

FIG. 16A shows the DNA sequence of rat peripheral myelin protein (SEQ ID NO: 7) and deduced amino acid sequence (SEQ ID NO: 3);

FIG. 16B shows a comparison of rat peripheral myelin protein SR13 (SEQ ID NO: 3) and mouse Gas-3 (SEQ ID NO: 8) amino acid sequences;

FIG. 16C shows a comparison of partial amino acid sequences of rat peripheral myelin protein SR-13 residues 1–17 (SEQ ID NO: 9) and residues 40–44 (SEQ ID NO: 10), bovine myelin PAS-II residues 1–17 (SEQ ID NO:5) and residues 40–44 (SEQ ID NO: 6), and mouse Gas-3 residues 1–17 (SEQ ID NO: 11) and residues 40–44 (SEQ ID NO: 12);

FIGS. 20A and 20B show PMP-22 derived peptides (SEQ ID NO: 13 and SEQ ID NO: 14) used to generate antibodies.

DETAILED DESCRIPTION OF THE INVENTION

I. Definitions

"PMP-22 protein" and "PMP-22 nucleic acid coding sequence" are, respectively, a protein and a nucleic acid sequence having substantial sequence identity, defined as at least about 80% sequence identity, with human peripheral myelin protein PMP-22 (SEQ ID NO: 2) and coding sequence (SEQ ID NO: 1) described herein.

Sequence identity, when referring to nucleic acid sequences in particular, will be considered to encompass non-identical codons which code for identical amino acids.

II. Isolation of a Rat PMP-22

Experiments performed in support of the present invention, described-below, demonstrate the cloning and expression of the rat SR13 cDNA, which encodes a myelin protein. This cDNA is related to the growth arrestspecific gens Gas-3, isolated from resting mouse 3T3 fibroblasts (see below).

A. Isolation and Regulation of SR13 mRNA

Figure 15:
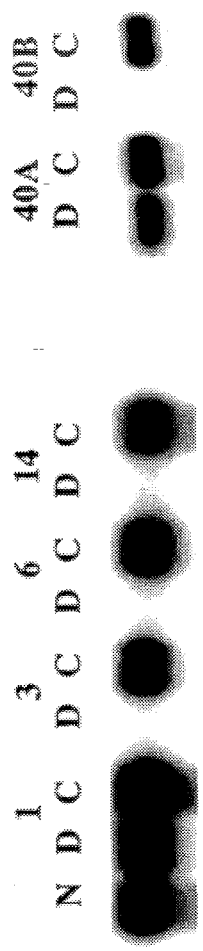
FIG. 15 shows a Northern blot of RNA isolated from rat sciatic nerve preparations blotted with rat peripheral myelin protein SR13 cDNA.

During the screening of a rat sciatic nerve cDNA library, an mRNA (SR13) was isolated that is abundantly expressed in sciatic nerve (representing 0.2% of the insert-containing library clones) and was strongly repressed following crush injury of the sciatic nerve. The longest SR13 cDNA insert (1.74 kilobases (kb)) was used to perform Northern blot analysis to determine its time course of expression during neuronal degeneration and regeneration (FIG. 15; Example 1). The SR13 transcript (1.8 kb) was partially repressed within 1 day after sciatic nerve injury and became <5% of normal levels from days 3 through 14. Forty days after the initial lesion (when the regeneration process was complete), the expression level of SR13 returned to close to normal (FIG. 1, lanes 40A). In contrast, if the nerve was cut and regeneration was prevented, SR13 was still downregulated at day 40 (FIG. 15, lanes 40B). The strong repression of this mRNA after sciatic nerve injury is strikingly similar to the patterns observed for the mRNAs encoding myelin Po and myelin basic protein (63,64).

B. Analysis of SR13 Sequence

The nucleotide sequence of the 1.74 kb SR13 cDNA insert is shown in FIG. 16. An open reading frame of 480 nucleotides was identified, which encodes a putative protein of 160 amino acids residues with a predicted molecular mass of approximately 18 kDa. Based on hydropathy plots and secondary structure predictions, amino acid residues 1–26, 67–88, 98–118, and 134–155 represent four hydrophobic, possibly membrane-associated domains. The N-terminal sequence possesses the characteristics of a signal peptide with the predicted cleavage site at Ser-26/Gln-27 (according to the algorithm of von Heijne, (65)).

There is a single consensus site for N-linked glycosylation at Asn-41. Comparison of the cDNA sequence to the GenBank data base (66) suggests that the SR13 mRNA has homology to the growth arrest-specific mRNA (Gas-3), which was isolated from serum-starved 3T3 mouse fibroblasts (67,68): FIG. 16B shows sequence divergence at the C-terminus.

C. Expression of SR13 mRNA in Different Tissues

Figure 17:
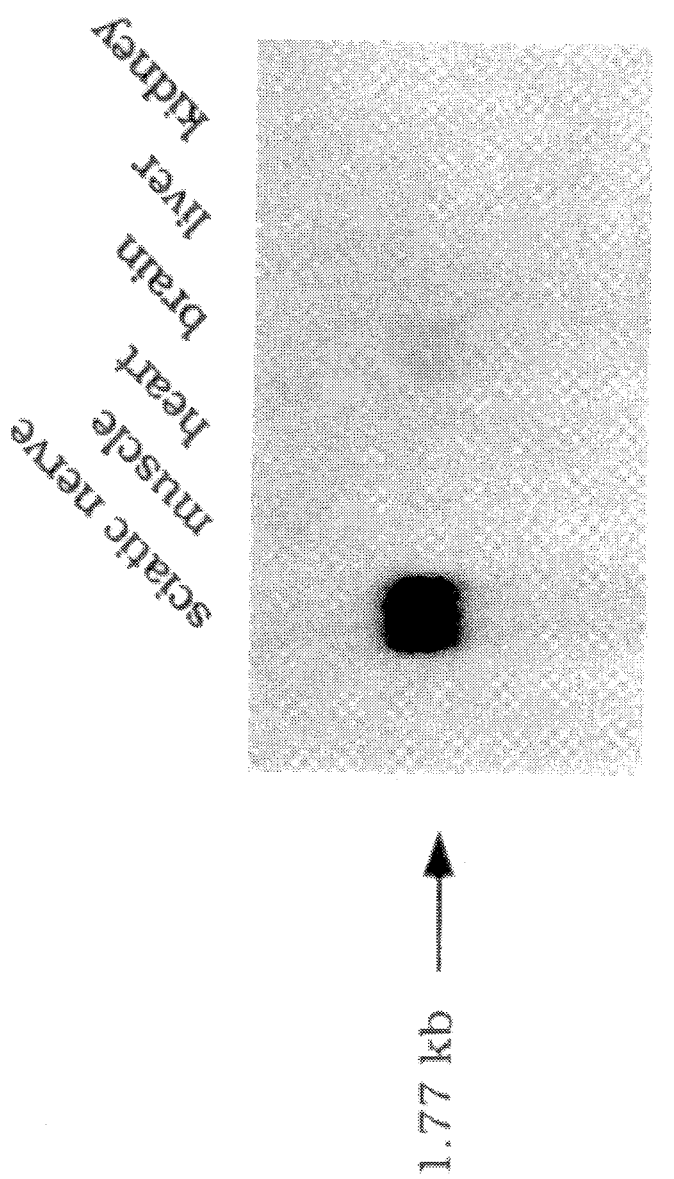
FIG. 17 is a Northern blot of total RNA isolated from rat tissues, using a rat SR13 cDNA probe.

SR13 was strongly expressed in sciatic nerve as a 1.8 kb transcript, whereas a weak signal was detected in brain tissue (FIG. 17). Heart and muscle show traces of SR13-specific mRNA after prolonged exposure, probably reflecting the strong innervation of these organs.

D. Expression of Recombinant SR13 Protein in COS-7 Cells

Figure 18:
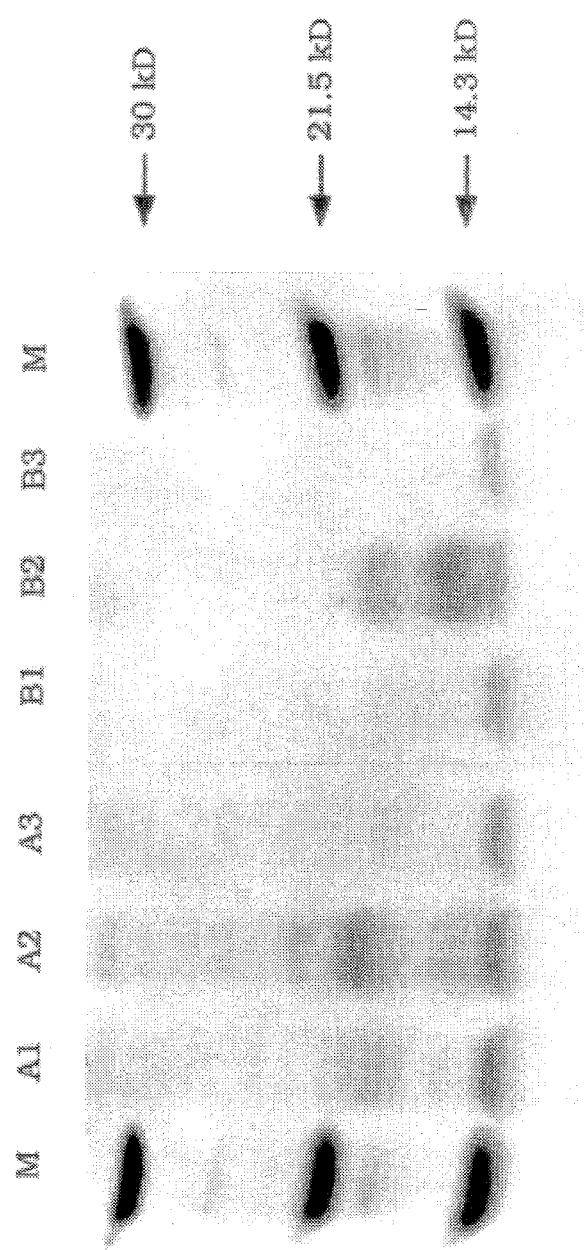
FIG. 18 shows recognition of COS cell expressed SR-13 protein by antiserum to rat myelin.

The SR13 cDNA was inserted into the eukaryotic expression vector CDM8 and transiently expressed in COS-7 cells. Transfected cells were metabolically labeled, lysed, and immunoprecipitated with a polyclonal antiserum directed against purified peripheral nerve myelin. An approximately 19 kilodalton (kDa) protein was specifically detected in SR13-transfected COS cells (FIG. 18, lane A2). No labeled proteins were precipitated from either SR-13-transfected COS cells incubated with normal rabbit serum or CDM8 (vector only)-transfected cells incubated with the specific antiserum (FIG. 18, lanes A1 and A3, respectively).

The presence of an N-glycosylation on the 19-kDa protein was substantiated by treating SR-13 transfected COS cells with the N-glycoslylation inhibitor tunicamycin. Under these culture conditions, the molecular mass of the 19-kDa protein was reduced to 15 kDa (FIG. 18, lane B2).

These results suggest that COS-7 cells both process the precursor to the mature protein (of molecular mass of approximately 15 kDa) and add N-linked sugars (to increase the molecular mass of approximately 15 kDa) and add N-linked sugars (to increase the molecular mass of the N-glycoslyated protein to approximately 19 kDa). The results also demonstrate that the SR13 cDNA, identified solely with a reverse-genetic approach, encodes an expressed protein in normal sciatic nerve.

E. Localization Of SR13-Like Immunoreactivity in Rat Sciatic Nerve

The SR13-encoded protein is precipitated by a myelin-specific antibody. Further, using polyclonal rabbit antisera raised against peptides derived from the cDNA-predicted SR13 amino acid sequence in an immunohistochemical analysis, intense immunoreactivity was localized to the myelin sheath of the sciatic nerve (FIG. 19A) in a pattern indistinguishable from the staining observed with antisera against myelin basic protein. No immunoreactivity was detected in axons and connective tissue support cells. Skeletal muscle was also unstained except for innervating myelinated fibers, explaining the weak SR13-specific signals observed in Northern blots. Identical results were obtained from different regions of the SR13 protein.

F. The SR13 Protein

The SR13 protein is a myelin protein based on the following evidence. First, the SR13 mRNA shows a similar time course of down-regulation after sciatic nerve injury as observed for the mRNAs encoding the classical myelin proteins $P_o$ and myelin basic protein. Second, the recombinant SR13-encoded protein expressed in COS cells is specifically recognized by an antiserum raised against preparations of purified peripheral nerve myelin. Finally, SR13-specific antipeptide antibodies localize the SR13 protein to the myelin sheath of the sciatic nerve.

Further evidence emerges from a comparison of the partial amino acid sequence of the previously described myelin protein PAS-II (69) and SR13. Two separate regions comprising a total of 22 amino acids of the PAS-II protein have been sequenced (70). These sequences share 80% identify with the SR13 protein (FIG. 16C). PAS-II was isolated from purified myelin of various species (69) and shows the same developmental pattern of expression in the chicken sciatic nerve as other major myelin proteins (71).

Experiments performed in support of the present invention have lead to the characterization of the SR13 protein. These studies demonstrate that SR13 is an approximately 22 kd myelin protein which is expressed predominantly in the PNS. Accordingly, this protein has been designated peripheral myelin protein 22 (PMP-22).

III. Isolation of Mouse PMP-22

The autosomal dominant trembler mutation (47) (Tr), genetically mapped to mouse chromosome 11 (48), is manifested as a Schwann cell defect, characterized by severe hypomyelination (50) and continuing Schwann cell proliferation (51, 52). Affected animals move clumsily and develop tremor and transient seizures at a young age. A potential growth regulating novel myelin protein PMP22 (53, 54), which is expressed by Schwann cells is found uniquely in peripheral myelin.

The cloning and expression of the novel myelin protein PMP-22/SR13 has been reported (53, 54). PMP-22 protein expression is restricted to the peripheral nervous system (PNS), whereas another major myelin protein, PLP, is restricted to the central nervous system (CNS). Both PMP-22 and PLP are predicted to be integral membrane proteins with four membrane-associated domains (refs 57, 58). Mutations in PLP were identified as the primary defect in hereditary CNS myelination diseases of mouse, dog and human (58).

As a first step in finding mutations that involving the PMP-22 gene, its chromosomal location in the mouse was mapped. PCR amplification of DNA from a standard Chinese hamster×mouse somatic cell hybrid panel (59), using PMP-22 specific PCR primers, did not yield specific products. These hybrid lines contain overlapping sets of all mouse chromosomes except for chromosome 11. A positive signal for mouse-specific PCR-AccI fragments (FIG. 9; Example 6) in the rat×mouse hybrid cell line RTM9, which contains only two mouse chromosomes, 11 and 13, fused together, confirmed the assignment of PMP-22 to chromosome 11.

Figure 10:
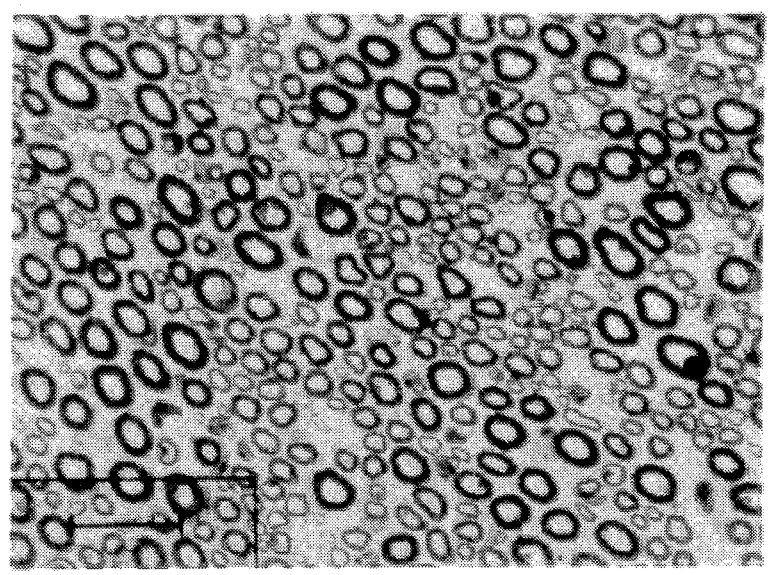
FIGS. 10A and 10B show transverse sections of sciatic nerves from a wild-type (+/+.
Figure 10:
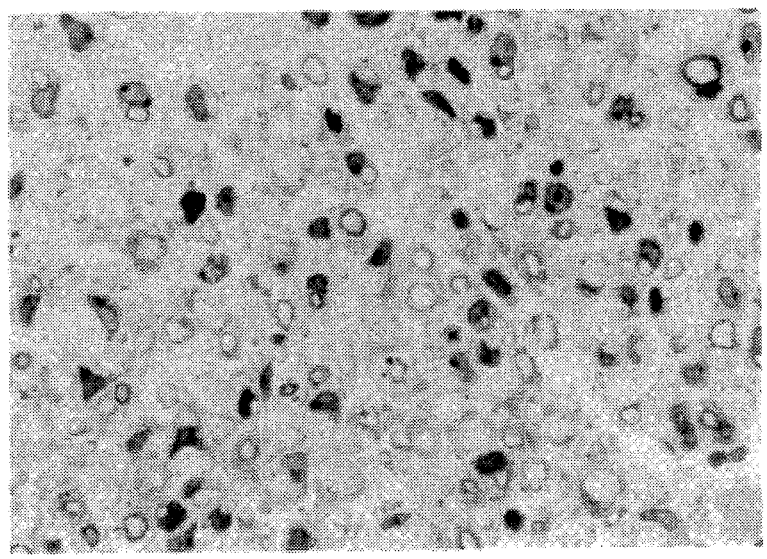

Two classes of PMP-22 cDNA were isolated by cloning specific PCR products from sciatic nerve RNA of behaviorally and histologically characterized heterozygous (Tir/+) mice (FIGS. 10A and 10B; Example 7). As determined by DNA sequencing, one group of cDNAs represented the PMP-22 wild type allele (FIG. 11A; Example 8). The second population of cDNAs, however, contained a single none-silent nucleotide exchange within the PMP-22 coding region (FIG. 11B; Example 8). The detected transition mutation from guanine (G) to adenine (A) leads to the substitution of an aspartic acid residue for a glycine residue in the PMP-22 protein (FIG. 13; Example 9). Direct sequencing of products of two independent PCR amplifications on reverse transcribed sciatic nerve RNA confirmed the presence of both PMP-22 alleles in heterozygous (Tir) mice (FIG. 11C; Example 8). The G to A base change introduces a novel EcoRV restriction endonuclease cleavage site in the mutated PMP-22 gene. This finding was exploited in a double-blind analysis of three Tir/+ mice and three unaffected wild type +/+ animals from the same litter, born to a Tir/+ female mated to a (C57BL/6J×C3HeB/FeJ)F$_1$+/+ male at the N7 generation of outcrosses to the wild type F1 hybrid stock. Using direct amplification of genomic DNA followed by EcoRV digestion, the mutated and wild type PMP-22 allele were found in all three Tir/+ mice, while the three normal litter mates carried only the wild type allele (FIG. 12; Example 8). Since the mice were used at the N7 generation of inbreeding, the transition mutation in the PMP-22 gene maps with high probability to the immediate vicinity of the Tr locus on chromosome 11.

The predicted effect of a mutation in the PMP-22 protein is consistent with the phenotype of the Tr mouse and recent studies on PMP-22. First, the PMP-22 protein is expressed predominantly by Schwann cells of the PNS and is not detectable in the CNS. In agreement, the Tr mutation is manifested as a Schwann cell defect in the PNS with no consequences observed in the CNS. Second, the PMP-22 protein is localized in the compact PNS myelin sheath. In accord, markedly reduced myelination of PNS axons is found in Tr mutants (FIGS. 10A and 10B; Example 7). Third, PMP-22 mRNA expression is implicated in cellular growth arrest (57): the abnormality of PMP-22 may explain the persistence of Schwann cell proliferation into adulthood in Tr animals.

The above results describe the identification of a critical, frame-shifting sequencing error in the previously reported sequence of gas3 CDNA (57), the putative mouse homologue of rat PMP-22. Experiments performed in support of the present invention provide results which clarify that the correct mouse (FIG. 13; Example 9) and rat PMP-22 amino acid sequences (56) share identical lengths and an amino-acid identity of 97.5%.

Figure 4:
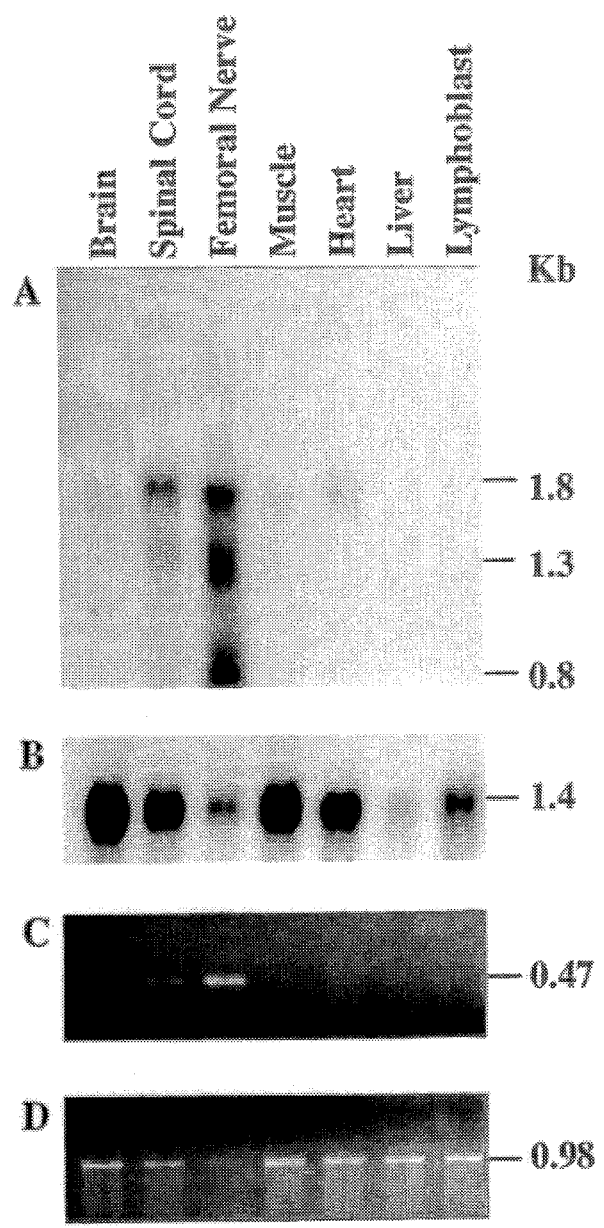
FIG. 4A shows a Northern blot of human RNA extracted from human brain, spinal cord, femoral nerve, skeletal muscle, heart, liver and lymphoblasts in consecutive lanes using as a hybridization probe a PMP-22 cDNA probe.
FIG. 4B shows Northern blot of the same tissue samples as in FIG. 4A, in which glyceraldehyde-3-phosphate dehydrogenase gens (G3PDH) was used as a control probe.
FIG. 4C shows RT-PCR analysis of human RNAs using primers specific for the PMP-22 cDNA.
FIG. 4D shows RT-PCR analysis as in FIG. 4C, using primers specific for G3PDH cDNA.

The mutation reported here in the PMP-22 gene translates into the replacement of glycine$^{150}$ by aspartic acid$^{150}$ in the PMP-22 polypeptide (FIG. 4A). This exchange introduces a charged amino acid in the fourth putative transmembrane-spanning domain of the PMP-22 protein (FIG. 14; Example 9). Such a mutation is likely to affect the structure and function of an integral membrane protein. Alternatively, this point mutation may interfere with the specific function of a critical domain of the PMP-22 protein. In this context, it is of interest that similarly positioned, deleterious mutations were found in the PLP gene (58).

The data presented above indicate that a non-conservative amino-acid substitution in the PMP-22 protein is likely responsible for the Tr phenotype. Additional evidence for the involvement of PMP-22 in peripheral neuropathies can be anticipated from an analysis of the primary structure of PMP-22 in the Tr$^1$ mouse, a mutation allelic to Tr (51). These results suggest that analysis of corresponding human genes is important for understanding of the basis of selected human inherited PNS neuropathies (see next section).

III. Isolation of Human PMP-22

A. Charcot-Marie-Tooth Disease

Charcot-Marie-Tooth disease (CMT) is a common inherited peripheral neuropathy in humans involving both motor and sensory nerves (1,2,3). This disease has a prevalence rate of 1 in 2500 (4). The prevalent subtype of CMT, CMT type 1A (CMT1A), is clinically characterized by distal muscle atrophy and weakness, decreased nerve conduction velocity (NCV), and hypertrophic neuropathy (2). Genetically, CMT1A is inherited in an autosomal dominant fashion and has been shown associated with a submicroscopic duplication involving more than 1 megabase (Mb) of sequence on the short arm of chromosome 17 (3,5–8).

Molecular analysis of CMT1A patient genomes has shown that the sequences duplicated are contained entirely within the large duplication region (5). These data supports a model for gene dosage effect as a mechanism for CMT1A involving overexpression of one or more genes mapping within the duplicated region.

As described above, PMP-22 protein (peripheral myelin protein-22) is a potentially growth-regulating 22 kDa protein, which is expressed by Schwann cells and is localized mainly in compact peripheral nervous system (PNS) myelin in rat (16). Trembler (Tr) and trembler J (Tr_$^J$) in mice carrying mutations in two distinct putative membrane domains of PMP-22 exhibit severe myelin deficiencies in the peripheral nervous system and continued Schwann cell proliferation throughout life (10,17,18). These features resemble the neuropathology seen in CMT1A patients.

B. Cloning of a Human PMP-22 cDNA

The human PMP-22 CDNA was cloned and analyzed by a combination of CDNA library screening and PCR technology (FIG. 1; Example 10). The longest open reading frame of the human PMP-22 cDNA predicts a polypeptide of 160 amino acids. Comparison of deduced amino acid sequences of human, rat, mouse and bovine PMP-22 proteins indicates a very high degree of evolutionary conservation (FIG. 2 (A–D); Example 10). There is 87% identity between human and rat PMP-22 and 86% identity between human and mouse PMP-22. In particular, a consensus sequence for N-linked glycosylation (amino acid position 41), shown to be functional in vivo (19) and in vitro (20,21), is conserved in all four species.

Predicted membrane-associated regions of the PMP-22 protein are especially highly conserved, suggesting a possible functional role of these domains.

C. Mapping of the PMP-22 Gene within the Duplication Interval

Figure 3:
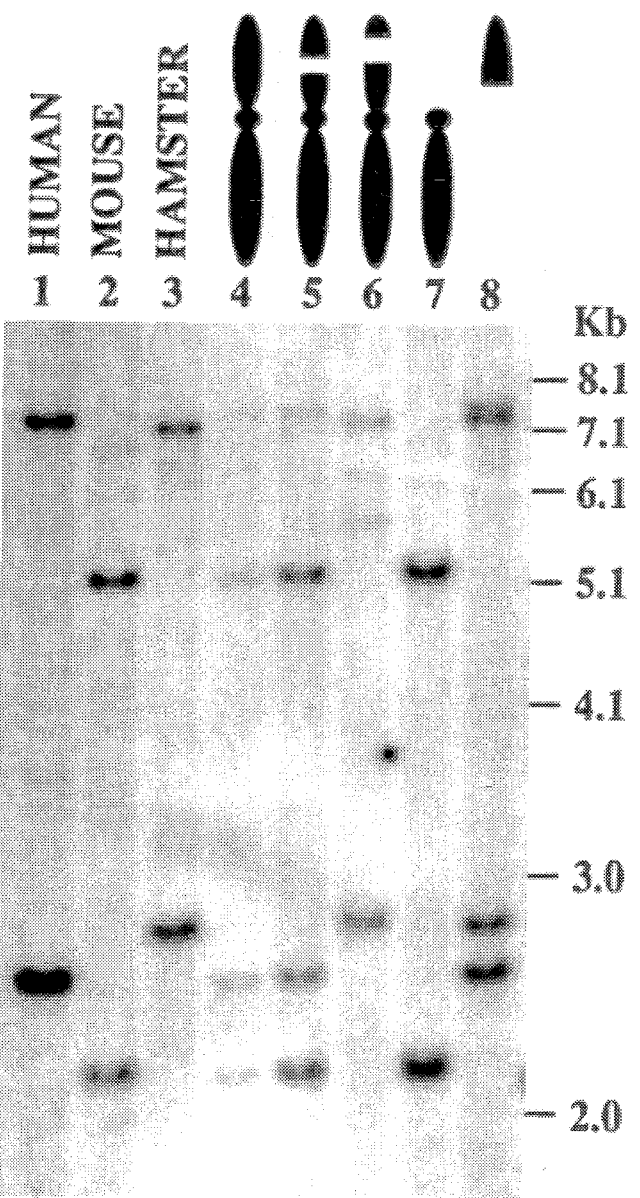
FIG. 3 shows a Southern blot of HindIII digested genomic DNA derived from a human control individual (lane 1, human), a mouse TK cell line (lane 2, mouse), the hamster HPRT cell line RJK88 (lane 3, hamster) and cell hybrids MH22-6 (lane 4), HY254-1 (lane 5), HY357-2D (lane 6), LS-1 (lane 7) and 88H5 (lane 8) retaining portions of human chromosome 17, using as cDNA hybridization probe phPMP22-1.

The chromosomal location of the PMP-22 gene was determined using somatic cell hybrid mapping panels. Preliminary PCR-based studies assigned the PMP-22 gene to human chromosome 17, and specifically to the 17p11.2-17p12 region. These results were confirmed by Southern analysis of HindIII digested DNA from the somatic cell hybrid panel using the human PMP-22 cDNA as a probe (FIG. 3; Example 11). Two genomic HindIII fragments of 7.4 kb and 2.5 kb were detected in human DNA which were only present in somatic cell hybrids retaining the 17p11.2 - 17p12 region. In particular, the hybrids Hy254-1 and Hy357-2D (22) which have distal breakpoints in 17p11.2 and 17p12, respectively, played a key role in mapping PMP-22 to the duplication region in CMT1A patients. The hybrid Hy357-2D is deleted for all of the markers duplicated in CMT1A patients (22) and did not retain human PMP-22 sequences (lane 6, FIG. 3; Example 11) whereas the hybrid Hy254-1 which contains the CMT1A region retained these sequences (lane 5, FIG. 3; Example 11).

D. Expression Analysis of Human PMP-22

The pattern of expression of the human PMP-22 gene was determined by northern analysis (Ausubel, et al.) of RNA from various human tissues using a cDNA probe, FBR1. Three transcripts of approximately 1.8 kb, 1.3 kb and 0.8 kb were detected in the spinal cord and the femoral nerve (FIG. 4A; Example 12). Trace amounts of the 1.8 kb transcript were found in the brain, and in the skeletal muscle and heart possibly due to innervation of the latter tissues. Hybridization of the same northern blot to the cDNA for the ubiquitously expressed glyceraldehyde 3-phosphate dehydrogenase (G3PDH) gene was used to confirm the integrity of the mRNA and to obtain a measure of the amounts of RNA loaded on the gel (FIG. 4B; Example 12). This control experiment indicated underloading of the lane with the femoral nerve RNA sample and accentuated the observation that PMP-22 mRNA is abundantly expressed in this tissue.

The expression patterns of the PMP-22 gene and of the control G3PDH gene were further assayed by reverse transcription-polymerase chain reaction (RT-PCR) amplification of the PMP-22 cDNA using the various RNAs as templates (FIG. 4C and 4D; Example 12). These results confirm that the PMF-22 gene is expressed at high levels only in the peripheral nerve and spinal cord identical to previous PMP-22 expression studies in the rat (16,21).

E. Genomic Clones Spanning the Human PMP-22 Locus

To isolate genomic clones spanning the PMP-22 gene, a gridded cosmid library constructed from flow-sorted chromosome 17 was screened with several probes representing the PMP-22 gene. Eight unique positively hybridizing cosmids were identified and used to establish an EcoRI restriction map of the PMP-22 gene region (FIG. 5; Example 13). Three EcoRI fragments of 11 kb, 8.2 kb and 4.9 kb hybridized to the PMP-22 cDNA. Parts of the 5' untranslated region of the gene were localized to the 11 kb EcoRI fragment by sequencing of the subclone p132-G8R1 containing this fragment.

A 4.5 kb EcoRI fragment immediately upstream of the 11 kb EcoRI fragment was also subcloned (p132-G8R5) and shown to retain a portion of the CpG-rich island associated with the PMP-22 gene (see below).

F. Fluorescence in situ Hybridization and RFLP Analysis: Evidence that the PMP-22 Gene is Duplicated in CMT1A Patients.

Fluorescence in situ hybridization of interphase nuclei from CMT1A and control individuals was previously used to demomtrate the duplication in CMT1A patients (3). The cosmid c132-GB containing a portion of the 5' region of the PMP-22 gene and a control cosmid c1516 mapping outside the CMT1A duplication but within 17p11.2 were used for similar studies. Two-color FISH (3, 46) analysis was performed on interphase nuclei from synchronized lymphoblasts of a control individual 76–289, and a severely affected CMT1A patient 42–333 previously shown to be homozygous for the duplication mutation (3). The results of this analysis show that the PMP-22 sequences are present in one copy on each of the chromosomes 17 of the control individual (FIG. 6A; Example 14) and in two copies on both chromosomes 17 of the homozygous CMT1A patient (FIG. 6B; Example 14).

Dosage differences in MspI RFLPs associated with the markers VAW409R3 and VAW409R1 had been previously demonstrated in CMT1A patients (3,6,7). To identify polymorphisms within the PMP-22 gene which might be useful to demonstrate similar dosage differences, DNA from 13 unrelated CMT1A patients and five control individuals were subjected to Southern analysis after digestion with AvaII, BanI, BanII, BclI, BglI, BglII, DraI, EcoRV, HincII, MboI and RsaI using the cosmid c132-G8 as a probe. A HincII RFLP was identified within the PMP-22 gene. To ensure reliable discernment of dosage differences of the polymorphic alleles in CMT1A patients, double digests were performed with EcoRI and HincII to reduce the size of the polymorphic alleles. Polymorphic alleles of 11 kilobases (kb) and 9.6 kb were observed in EcoRI/HincII digested DNA hybridized to the p132-GBRI fragment.

Figure 7:
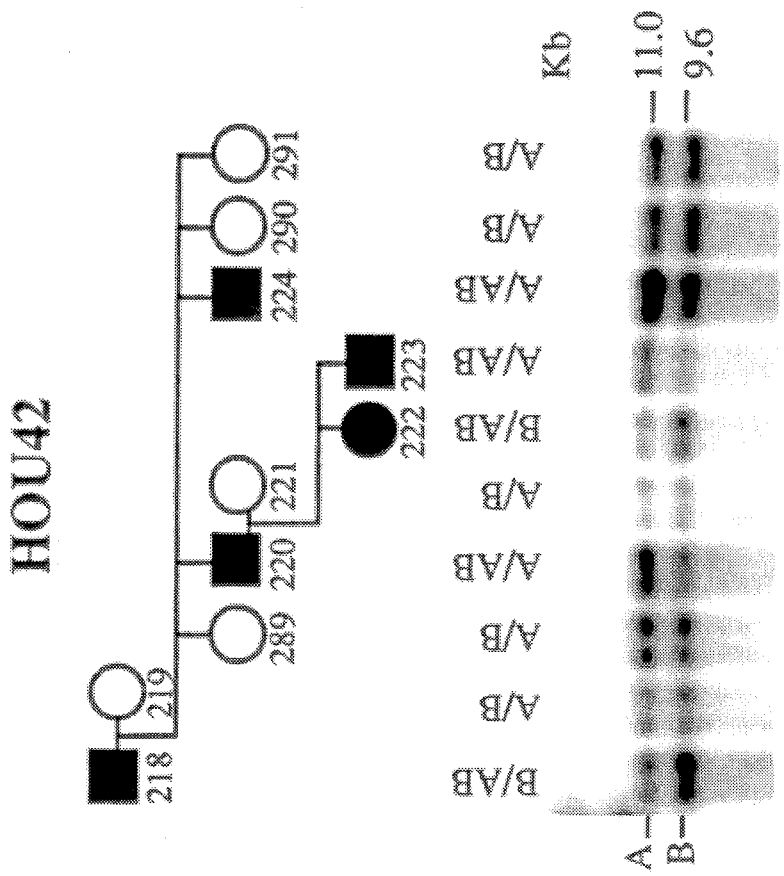
FIG. 7A shows a diagram of Mendelian inheritance of dosage differences of polymorphic alleles at the hpmp locus in a CMT1A nuclear family.
FIG. 7B shows Southern blots of HincII and EcoRI digested genomic DNA from the individuals within the nuclear family represented in the diagram of FIG. 7A, using as probe the cosmid p132-G8R1, labeled with allelic genotypes A and B.

FIG. 7B (Example 15) shows a Southern analysis of EcoRI/HincII digested DNA from a CMT1A nuclear family with the probe p132-G8R1. Dosage differences of the polymorphic alleles are detected in CMT1A patients and not in unaffected individuals. Furthermore, the segregation of alleles demonstrates mendelian inheritance of a disease chromosome which carries both an A and a B allele in affected individuals of this particular family (FIG. 7A; Example 15). This restriction fragment length polymorphism (RFLP) will be useful in conjunction with other RFLPs associated with markers within the duplication interval for the diagnosis of CMT1A patients with the duplication mutation or other markers associated with mutations affecting restriction sites, such as substitution and deletion mutations.

G. Fine Mapping of the PMP-22 Gene within the CMT1A Duplication Interval

Two additional novel restriction fragments of 500 kb each were detected by the restriction enzymes FspI (5) and AscI (this study) only in CMT1A patients. The AscI fragment is only evident in partially digested patient DNA. In order to determine the relative position of the PMP-22 gene with respect to these novel restriction fragments observed in CMT1A patients, as well as the location of the gene within the physical map of the duplication interval, pulsed field gel electrophoresis (PFGE; 3, 46) was performed using sample DNA from a patient and a control (FIG. 8A; Example 16). The probe used in panel A was a 3.7 kb EcoRI/HindIII fragment containing the third exon of the PMP-22 gene. The pattern of hybridization with this probe as well as several other segments of the PMP-22 gene including a 10 kb FspI/EcoRI fragment from p132-G8R1 and the entire cosmid c103-B11 were similar and did not reveal any novel fragments in DNA from the CMT1A patient.

Figure 5:
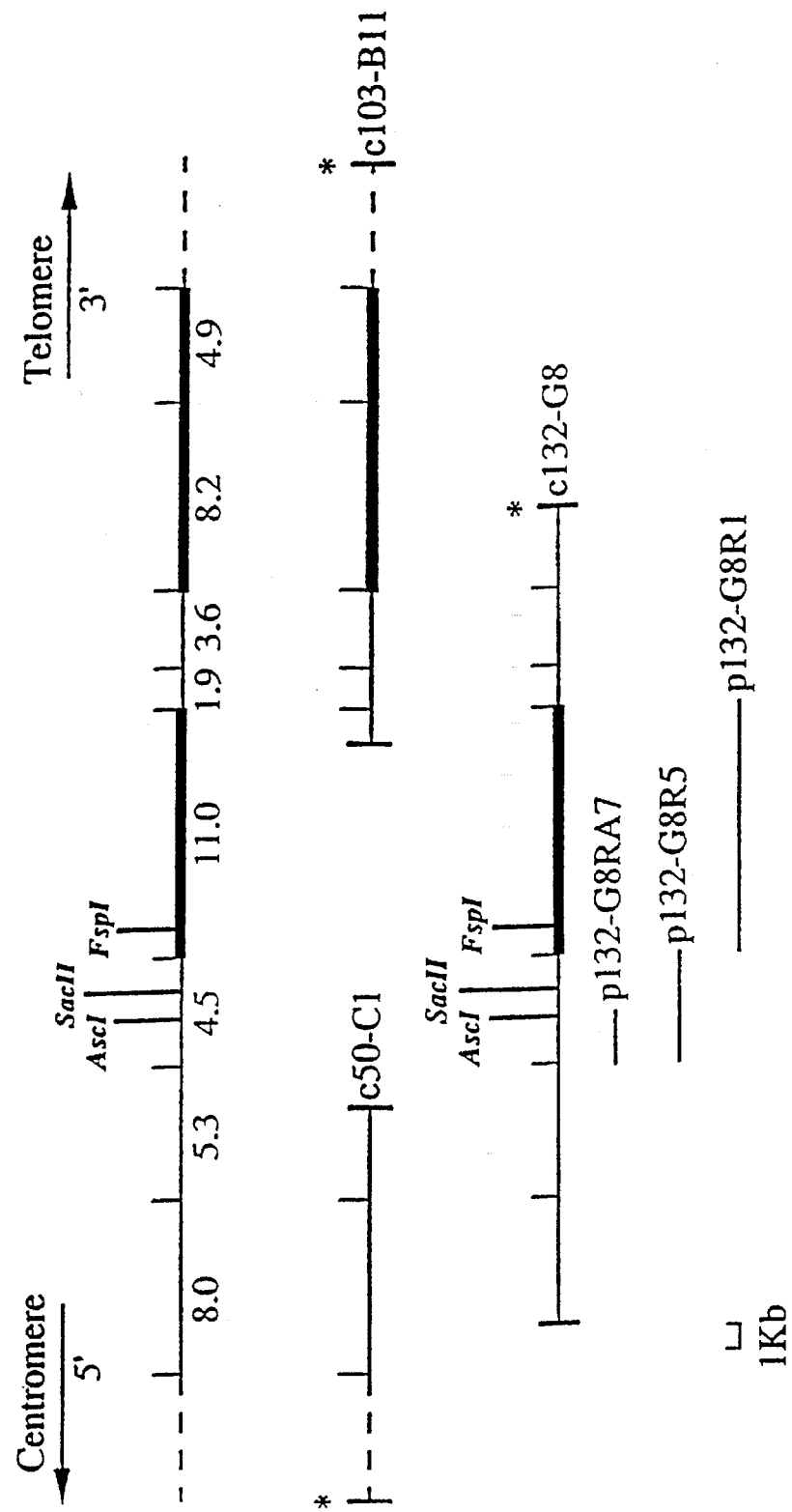
FIG. 5 shows diagrams of a cosmid contig constructed for the PMP-22 genomic region by identification of overlapping cosmids c59-C1, c103-B11, c132-G8, p132-G8RA7, p132-G8R5, and p132-G8R1 from a cosmid library constructed from human genome 17 where bold lines indicate fragments showing hybridization to the cDNA; thin vertical lines represnt EcQRI sites, asterisks indicate the position of the T3 polymerase sequence in the vector, and dotted lines indicate where the EcoRI restriction map is not available.

However, when a 2.2 kb EcoRI/AscI fragment (p132-G8RA7; FIG. 5; Example 13) located immediately upstream of the PMP-22 gene was used as a probe, it detected the novel CMT1A-specific SacII, FspI and AscI fragments alluded to above (FIG. 8B; Example 16). The same Southern blot was hybridized to the probe VAW409R3 (D17S122), which had been used to initially identify the duplication, and a pattern identical to that seen in panel B was observed.

Figure 8:
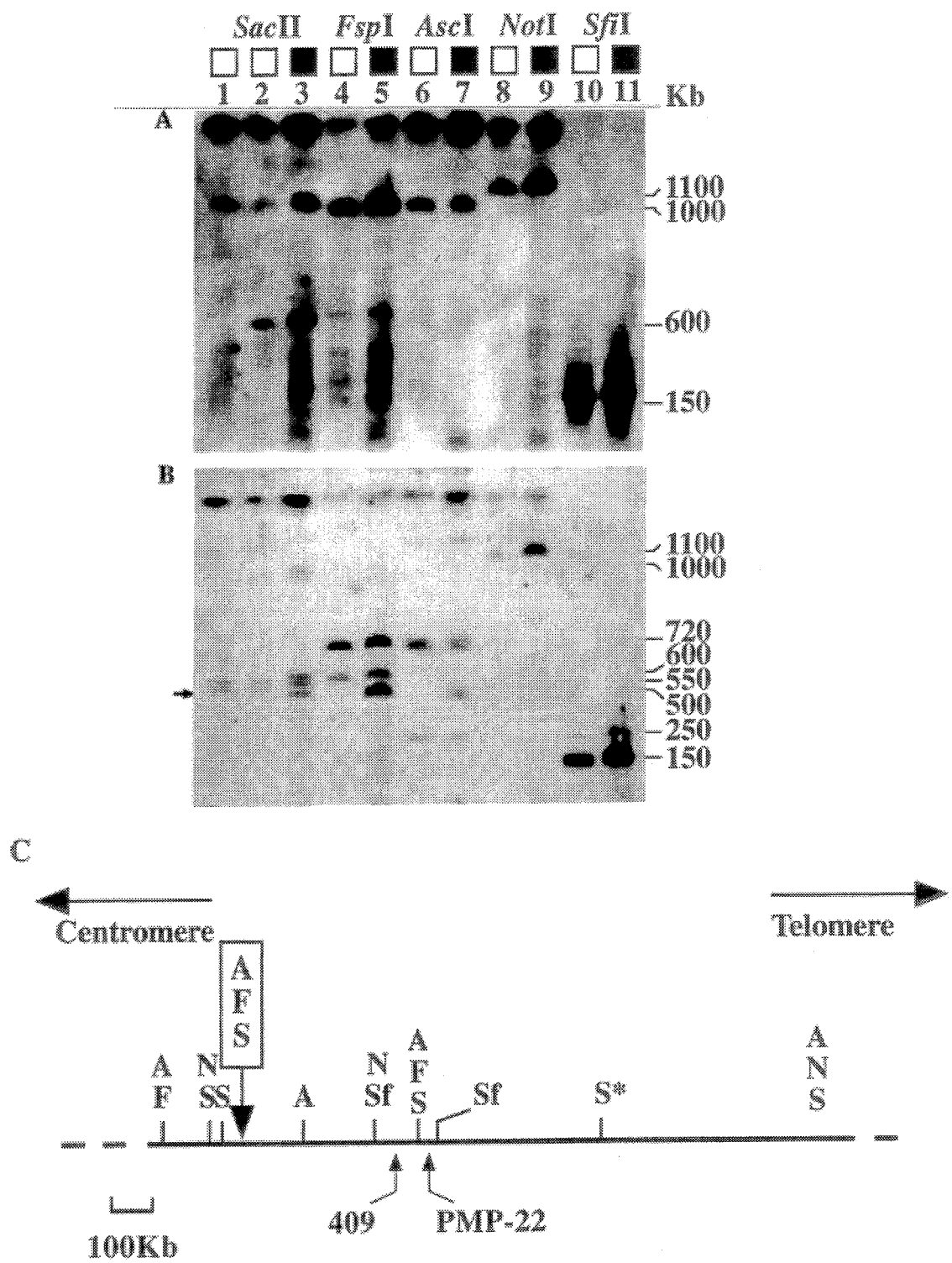
FIGS. 8A and 8B show pulsed field analyses of genomic DNA from lymphocytes of control and CMT-1A individuals using the probe p103-B11RH4 (FIG. 8A) and with probe p132G8-RA7 (FIG. 8B), where lane 1 DNA is from a control male SD, lanes 2,4,6,8,and 10 are from control male MM, lanes 3,5,7,9, and 11 are from CMT1A patient HOU1-3.
FIG. 8C shows a pulsed field of the hpmp and VAW409 regions deduced from the hybridizations shown in FIGS. 8A and 8B.

A pulsed field map was constructed on the basis of the above data and is shown schematically in FIG. 8C (Example 16). The probe VAW409R3 and PMP-22 gene-specific probes hybridize to the same 150 kb SfiI fragment indicating the close physical proximity of these markers. These data are consistent with the PMP-22 gene being located entirely within the CMT1A duplication. The location of the novel SacII, AscI and FspI sites in CMT1A patients deduced from the PFGE studies provides a rough estimate of the duplication junction being less than or equal to 500 kb from the PMP-22 locus.

H. The Human PMP-22 Coding Region

The Tr mouse has been considered an animal model for CMT1A based on its neuropathological phenotype (14,15, 23) and its location on mouse chromosome 11 near the homologous region for proximal human chromosome 17p (12). Mutations in the mouse peripheral myelin protein gene PMP-22 have been proposed to be responsible for the Tr and $T\_^j$ phenotypes (14,15; see above). In support of this hypothesis, the mouse PMP-22 gene has been mapped to the genetically defined Tr locus. The above data support the mapping of the human PMP-22 gene to human chromosome 17p11.2 - 17p12, thereby extending the conservation of genes on mouse chromosome 11 and human chromosome 17 and supporting PMP-22 as a gene for CMT1A.

The identification of the first coding exon of the PMP-22 gene within the 11 kb EcoRI fragment in c132-G8 as well as the map shown in FIG. 8C (Example 16) suggest that the PMP-22 gene is not interrupted in CMT1A patients. Furthermore, previous findings demonstrating duplication of markers VAW409R3 (D17SI22) and VAW412R3 (D17S125) in CMT1A patients (3,6,7) which are located approximately 50 kb and approximately 1 kb upstream and downstream, respectively of the PMP-22 gene (unpublished results) suggest that the PMP-22 gene is located entirely within the duplication.

Northern analysis with the human PMP-22 cDNA identified three transcripts of approximately 1.8, 1.3 and 0.8 kb in peripheral nerve and spinal cord. Previously, a single transcript of 1.8 kb had been identified in the sciatic nerve and spinal cord of the rat (16,21).

The Tr and CMT1A phenotypes are strikingly similar. Both the Tr mutation and CMT1A show autosomal dominant inheritance and are manifested pathologically as a marked decrease in the degree of myelination and a number of large caliber axons in the peripheral nervous system, resulting in severely reduced nerve conduction velocities (24–27). Hypertrophic peripheral nerve changes in both disorders include increased numbers of Schwann cell nuclei, the formation of "onion bulbs" consisting of supernumerary Schwann cell processes, and increased collagen deposition surrounding axons (10, 25–27).

In Tr nerves, the primary defect apparently resides in myelinating Schwann cells (28) whereas in CMT1A, both Schwann cell and neuronal defects have been individually implicated (27). The observation of small axon diameters with altered axon/myelin ratios that are suggestive of a primary axonopathy in CMT1A patients supports the hypothesis that CMT1A is primarily a neuronal defect (27,29,30).

However, recent studies on hypomyelinating Tr mice, in which Tr nerve segments were grafted into normal mice, have shown that the expression of the mutated PMP-22 allele, is restricted to Schwann cells (16). This expression is sufficient to cause axonal abnormalities, which include small axon diameters, increased neurofilament density, and alterations in the phosphorylation of neurofilament protein (31).

Experiments performed in support of the present invention indicate that the CMT1A mutation involves a chromosomal duplication of about 1.5 mB in the majority of patients. This result and the data presented above support a model of gene dosage as a mechanism for CMT1A.

The present data show that the human PMP-22 gene is contained entirely within the CMT1A duplication supporting that dosage differences in PMP-22 expression are partially or entirely responsible for CMT1A. Point, substitution or deletion mutations may contribute to some manifestations of CMT1A. The PMP-22 sequences of the present invention provide diagnostic means to examine the PMP-22 gene in number of patients for point or other subtle mutations.

Further, the above-data suggest that the PMP-22 gene maps within the duplication interval in CMT1A patients close to the marker D17S122 (VAW409) which had been previously associated with the CMT1A duplication (3,6).

The question of whether both abnormal PMP-22 expression and point mutations in the PMP-22 gene may lead to similar phenotypes is addressed in several ways. First, transgenic mice overexpressing the PMP-22 gene are created and examined for onset of peripheral neuropathy. In view of previous findings of homozygosity of the duplication mutation produces a very severe clinical CMT1A phenotype (3), transgenic mice overexpressing PMP-22 may be useful for testing threshold and dosage effects as well as tolerance to increased PMP-22 expression. Further, strategies for correction of the disease phenotype by normalizing the amount of PMP-22 gene product can be evaluated (5).

IV. Utility

This section describes examples some of the uses of oligonucleotide sequences to peripheral myelin protein, in the diagnosis and treatment of human hypertrophic neuropathies, and particularly, CMT type 1A.

A. Diagnostics

The use of probes that recognize gene sequences within the CMT duplication region of gene loci associated with CMT disease is described in co-pending parent U.S. patent application Ser. No. 07/711,615, filed Jun. 6, 1991, which is incorporated herein by reference. It can be appreciated that oligonucleotide probes generated using sequence information described herein can be used as reagents, to detect the presence of CMT duplication regions, in patients exhibiting symptoms of CMT. Patients who are found to have such duplicating regions are sometimes referred to as "duplicating patients."

Using the sequence information provided herein, it can be appreciated that non-duplicating patients and/or patients suspected of having mutations of a CMT locus of the genome, can be detected, using such techniques as oligonucleotide probe hybridization of DNA samples isolated from such patients, antibody recognition of myelin proteins expressed in such patients, and the like. That is, it is anticipated that probes and antibodies directed to the normal PMP-22 gene sequence and protein will exhibit detectably different binding properties when reacted with gene sequences and proteins containing mutations.

Additionally, it is appreciated that sequence information provided herein will be useful in the elucidation of specific mutations of the CMT locus, in those patients exhibiting such mutations. DNA isolated from CMT patients, and particularly non-duplicating CMT type 1A patients, is compared to normal DNA sequences, such as the human PMP-22 DNA sequence shown in FIG. 1, and mutations to the sequence are identified. Mutated regions of the DNA sequence are then used to design and produce reagents, such as oligonucleotide probes, specific to such regions. Likewise, CMT patient-derived DNA can be analyzed using RFLP analysis techniques, and the fragments generated compared to RFLP generated fragments from normal patients.

In addition it is expected that in some CMT patients, and especially in those patients exhibiting DNA mutations, PMP-22 will be produced having altered amino acid sequences. These altered sequences can be compared to normal sequences, and peptide regions encompassing altered regions of such proteins can be produced, using conventional means, to produce antibody reagents useful in the diagnosis of CMT. Antibodies produced against the normal as well as against the altered molecule can be used as immunocytochemical reagents.

In studies in support of the current invention, peptides have been synthesized from two hydrophilic regions of the PMP-22 sequence. These peptides are shown in FIGS. 20A and 20B. They have been used to generate polyclonal antisera in rabbits, as described (16). Such antibodies have found utility in staining of myelinated regions containing PMP-22 immunoreactivity in the peripheral nervous system.

B. Therapeutics

As described herein, it has been shown that a significant portion of patients exhibiting CMT-1A show DNA duplication of a portion of chromosome 17p and overexpression of PMP-22. In such patients, it can be appreciated that regulation of expression of the PMP-22, such as by anti-sense oligonucleotide treatment, is a potential means by which symptoms of PMP-22 overexpression can be ameliorated. Models for testing this therapeutic modality are described herein. Briefly, transgenic mice are produced which contain in their genome, an extra copy of the PMP-22 coding sequence. Anti-sense oligonucleotides, designed to form triplex structures with the PMP-22 coding sequence are then designed, according to methods known in the art, and are administered to the animal (Helene and Thuong, Genome 31: 413, 1989; Helene and Toulme, Biochim. Biophys Acta 1049: 99, 1990; Postel et al. Proc. Natl. Acad. Sci. USA 88 8227, 1991).

The following examples illustrate, but in no way are intended to limit the present invention.

MATERIALS AND METHODS

*E. coli* DNA polymerase I (Klenow fragment) was obtained from Boehringer Mannheim Biochemicals (BMB) (Indianapolis, Ind.). T4 DNA ligase and T4 DNA polymerase were obtained from New England Biolabs (Beverly, Mass.); Nitrocellulose filters were obtained from Schleicher and Schuell (Keene, N.H.).

Restriction enzymes and high/low RNA molecular size markers were purchased from Bethesda Research Laboratories (BRL). Chemicals were obtained from Sigma unless stated otherwise. $^{14}$C-labeled protein molecule size markers were purchased from Amersham.

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits were obtained from Boehringer-Mannheim Biochemical (BMB, Indianapolis, Ind.).

Oligonucleotide sequences encoding peptides can be either synthesized directly by standard methods of oligonucleotide synthesis, or, in the case of large coding sequences, synthesized by a a series of cloning steps involving a tandem array of multiple oligonucleotide fragments corresponding to the coding sequence (Crea; Yoshio et al.; Eaton et al.). Oligonucleotide coding sequences can be expressed by standard recombinant procedures (Maniatis et al.; Ausubel et al.)

Alternatively, peptides can be synthesized directly by standard in vitro techniques (Applied Biosystems, Foster City Calif.).

Common manipulations involved in polyclonal and monoclonal antibody work, including antibody purification from sera, were performed by standard procedures (Harlow et al. ). Pierce was a source of many antibody reagents.

General ELISA Protocol for Detection of Antibodies

Polystyrene 96 well plates Immulon II (PGC) is coated with 5 ug/mL (100 μL per well) peptide in 0.1M carb/bicarbonate buffer, pH 9.5. Plates are sealed with parafilm and stored at 4° C. overnight.

Plates are aspirated and blocked with 300 uL 10% NGS and incubated at 37° C. for 1 hr.

Plates are washed 5 times with PBS 0.5% "TWEEN-20".

Rabbit antisera are diluted in 0.1 M PBS, pH 7.2. The desired dilution(s) of antisera (0.1 mL) are added to each well and the plate incubated 1 hours at 37° C. The plates are then washed 5 times with PBS 0.5% "TWEEN-20".

Horseradish peroxidase (HRP) conjugated goat antirabbit antiserum (Cappel) is diluted 1/5,000 in PBS. 0.1 mL of this solution was added to each well. The plate is incubated 30 min at 37° C., then washed 5 times with PBS.

Sigma ABTS (substrate) is prepared just prior to addition to the plate.

The reagent consists of 50 mL 0.05 M citric acid, pH 4.2, 0.078 mL 30% hydrogen peroxide solution and 15 mg ABTS. 0.1 mL of the substrate is added to each well, then incubated for 30 min at room temperature. The reaction is stopped with the addition of 0.050 mL 5% SDS (w/v). The relative absorbance is determined at 410 nm.

Cell lines. Hybrids used for initial chromosomal assignment have been described previously (35,36). The panel used for regional assignment on chromosome 17 is as follows: hybrid MH22-6 contains a single chromosome 17 as the only human complement (37), Hy254-1 and Hy357-2D retain a del(17)(p11.2p11.2) and a del(17)(p11.2p12), respectively derived from patients with the Smith-Magenis syndrome (22,38), 88H5 contains 17pter-pl1.2 (37), and LS-1 contains 17cen-qter (39). The rodent parent of hybrids MH22-6, Hy254-1, and LS-1 was the mouse TK- cell line, Cl-1D, that of hybrid Hy357-2D was the hamster TK-cell line a23 and that of 88H5 is the hamster HPRT-cell line RJK88.

DNA Probes and Primers. The mouse cDNA probe PMP-22c contains 561 bp of the coding sequence (15). phPMP22-1 contains the human PMP-22 cDNA [position 147 to 820 (FIG. 1A)]in the vector TA-1000 (Invitrogen). FUSI is a 520 bp fragment of the human PMP-22 cDNA (position 800 to 1320) derived by PCR-amplification with human-specific primers. FBR1 is a 362 bp fragment of the human PMP-22 cDNA from position 171 to 532 derived by PCR amplification. For the RT-PCR experiments, PMP-22 specific primers were used to amplify a 470 bp region from position 171 to 640. Control primers that amplified a 983 bp region G3PDH mRNA were obtained from Clontech.

RNA Analysis. Human brain, spinal cord, and skeletal muscle samples were obtained 6 hours post-mortem from an 8 month infant who had expired from sudden infant death syndrome. Femoral nerve was obtained 22 hours postmortem from an 18 month female infant with congenital heart disease. Liver tissue was obtained from an infant undergoing a liver transplant procedure for ornithine transcarbamoylase deficiency. Heart tissue was obtained from a 10 year old female patient with dilated cardiomyopathy.

Total RNA was extracted from brain, heart, liver and lymphoblasts by guanidinium chloride/cesium chloride centrifugation (40), and from spinal cord, femoral nerve and skeletal muscle by the guanidinium isothiocyanate-phenol-chloroform method (41).

Northern analysis was performed by electrophoresis of approximately 5 ug of total RNA in 1.5% agarose gels containing formaldehyde (Maniatis, et al.; Ausubel, et al.).

RT-PCR was performed using 1 U each of AMV reverse transcriptase and Taq polymerase and 0.5 ug of total RNA in a reaction volume of 50 ul essentially as described previously (42).

Construction of a Cosmid Contig for the PMP-22 Region. Approximately 7500 cosmids representing a library constructed from flow-sorted chromosome 17 in the vector sCosl (Los Alamos National Laboratory) grown on gridded arrays of 384 on nylon filters (Genescreen Plus, NEN) were hybridized sequentially to the human PMP-22 cDNA probes, FUS1 and phPMP22-1, and to a mouse PMP-22 cDNA probe PMP-22c. Eight cosmids were identified. Partial EcoRI restriction digests of representative cosmids c103-E11 and c132-08 were electrophoresed in pulsed field gels and a restriction map constructed by hybridization to 13 and 17 polymerase promoter specific oligonucleotides as described by Evans et al. (43). Total EcoRI digests of all cosmids as well as a BamHI and BamHI/EcoRI digest of cosmid c103-B11 were used to confirm the accuracy of the restriction map.

EXAMPLE 1

Regulation of Expression of the SR13 mRNA During Sciatic Nerve Degeneration and Regeneration Total RNA was isolated by the method of Chomczynski and Sacchi (72) and examined by Northern blotting using "HYBOND" membranes (Amersham). Electrophoresis, transfer of RNA, and hybridizations were done as described (73). $^{32}$P-labeled SR13 cDNA probes were prepared by using a hexanucleotide labeling kit (Boehringer Mannheim). Total RNA (5 μg per lane) was analyzed by Northern blotting using the SR13 cDNA as a probe.

In FIG. 15, the numbers above the lanes refer to days after sciatic nerve crush. RNA was isolated from normal sciatic nerve (N) or after sciatic nerve injury from the distal segment of the ipsilateral (D) or contralateral (C) rat sciatic nerve. Lanes 40A and 40B, RNA isolated 40 days after crush injury (40A) or cut injury (40B).

EXAMPLE 2

Nucleic Acid Sequence and Amino Acid Homologies of SR13

A. DNA Manipulations and Sequence Analysis

Both strands of the SR13 cDNA insert were sequenced by the dideoxynucleotide chain-termination method (74) using a Sequenase kit (United States Biochemical) and double-stranded plasmid DNA as templates. Sequencing primers were either the T7 promoter primer, the CDM7 reverse primer (InVitrogen, San Diego, Calif.), or synthetic oligonucleotides from previously determined sequences. The sequences were analyzed by using the University of Wisconsin Genetics Computer Group programs (75). The homology to Gas-3 was identified by using the FASTA program to search the GenBank (Release 64.0), European Molecular Biology Laboratory (Release 23.0), and Swiss-Prot (Release 14.0) data bases; and the GAP program was used for alignment of sequences.

B. Nucliec Acid Sequence of the Rat SR13 cDNA

In FIG. 16A, solid underlined regions correspond to putative membrane-spanning domains, whereas the broken line indicates the putative signal sequence. A N-linked glycosylation consensus site is marked with an arrowhead.

C. Amino Acid Sequence Comparisons

Amino acid sequence (one-letter code) comparison of rat SR13 (top sequence) and mouse Gas-3 (bottom sequence) are presented in FIG. 16B. Identical residues are indicated by solid vertical lines, and conservative amino acid substitutions are shown by colons. FIG. 16C presents a comparison of partial amino acid sequences of bovine myelin PAS-II, rat SR13, and mouse Gas-3. Numbering refers to amino acid positions in the SR13 protein. X represents an undetermined amino acid residue in the PAS-II protein sequence.

EXAMPLE 3

Tissue distribution of rat SR13 mRNA

FIG. 17 shows the results of Northern blot analysis using RNA from the sources denoted in the figure. Isolation of the RNA was as described above. Each lane contains 10 μg of total RNA except for the sciatic nerve lane (2 μg of total RNA). mRNA sizes were determined by using RNA size markers. The probe was the SR13 cDNA, labeled as described above.

EXAMPLE 4

Immunoreactivity of the SR13 Protein

The SR13 cDNA in the CDM8 expression vector (76) was transfected into COS-7 cells by a modification of the DEAE-dextran/chloroquine method (77). Transfected cells were metabolically labeled with [$^{35}$S]cysteine (Amersham) for 3 hr and lysed in phosphate-buffered saline containing 1% Nonidet P-40, 1% deoxycholate, 0.1% SDS, and 2 mM phenylmethylsulfonyl fluoride. Labeled proteins were immunoprecipitated by using either normal rabbit serum or a rabbit polyclonal antiserum raised against purified rat sciatic nerve myelin. Immunocomplexes were formed using Pansorbin cells (Calbiochem). Precipitated proteins were eluted and analyzed on an SDS/12.5% polyarylamide gel under reducing conditions.

To inhibit N-linked glycoslyation, transfected COS cells were metabolically labeled in the presence of tunicamycin (10 μg/ml), lysed, and analyzed as described above.

The results of the above analysis are presented in FIG. 18. In the figure—Lanes A1–A3, SR13 protein expressed in COS cells is recognized by antiserum to rat myelin. Lane A1, COS were cells transfected with SR13 in the CDM8 expression vector, and proteins were immunoprecipitated with normal rabbit serum. Lane A2, proteins of the same transfected COS cells as in lane A1 were immunoprecipitated with the anti-sciatic nerve myelin serum. Lane A3, COS cells were transfected with the CDM8 vector only, and proteins were immunoprecipitated with the anti-sciatic nerve myelin serum. Lanes B1–B3, SR13 protein is N-glycoslyated in COS cells. Transfected COS cells were grown in the presence of tunicamycin. Lane B1, COS cells were transfected with SR13 in the CDM8 expression vector, and proteins were immunoprecipitated with normal rabbit serum. Lane B2, COS cells were transfected with SR13 in the CDM8 expression vector, and proteins were immunoprecipitated with the anti-sciatic nerve myelin serum. Lane B3, COS cells were transfected with CDM8 only, and proteins were immunoprecipitated with the antisciatic nerve serum, M, protein molecular size markers.

EXAMPLE 5

Peptide Antibodies and Immunohistochemistry

Two peptides corresponding to different hydrophilic regions of the cDNA-predicted SR13 protein sequence (FIG. 20) were synthesized on a Milligen/Biosearch automated peptide synthesizer, and rabbit antisera were raised (Harlow, et al.). Immunoperoxidase studies were performed on paraffin-embedded normal rat sciatic nerves fixed in 4% paraformaldehyde/0.1 M sodium phosphate, pH 7.4 by using the peroxidase, antiperoxidase method (78). Primary antisera were used at 1:150 dilutions.

Figure 19:
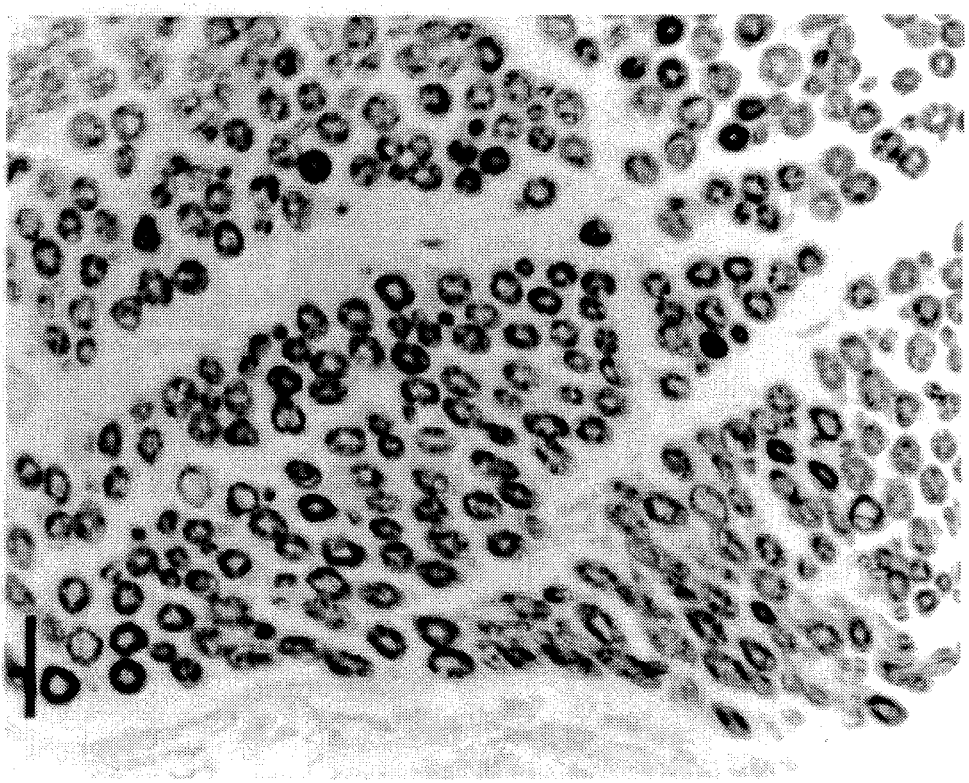
FIGS. 19A and 19B show immunohistochemical localization of SR-13 immunoreactive material in cross-sections of normal adult rat sciatic nerve stained with anti-SR13 peptide antiserum (FIG. 19A) or with peptide preblocked anti-SR13 peptide antiserum (FIG. 19B)
Figure 19:
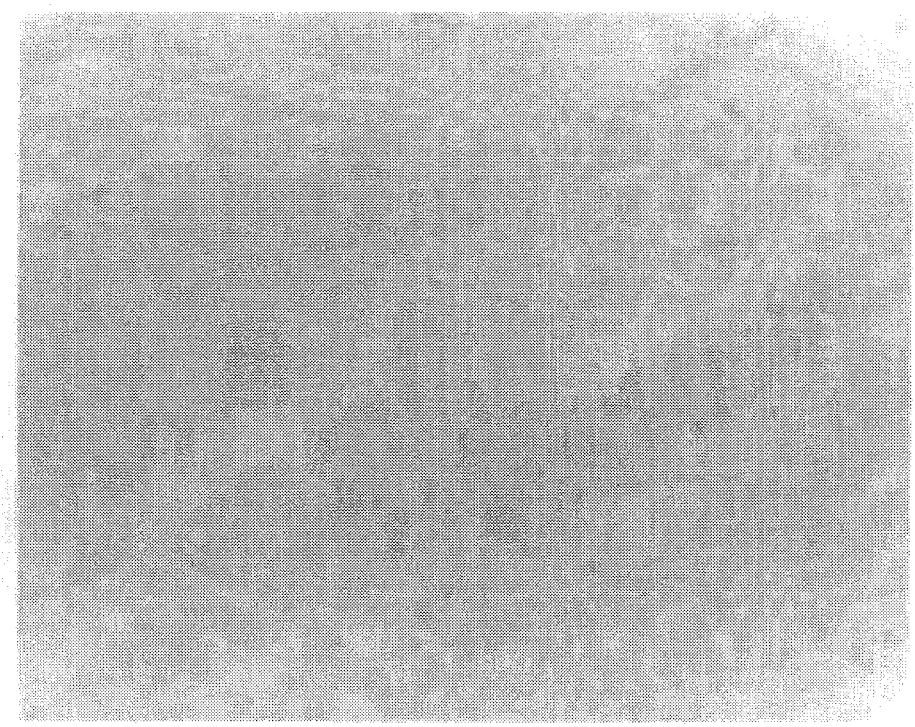

Immunohistochemical localization of SR13-like immuno-reactivity in cross sections of normal adult rat sciatic nerve were performed. The cross sections were stained with anti-SR13 peptide antiserum (FIG. 19A) or with a peptide-preblocked anti-SR13 peptide antiserum (FIG. 19B). Each darkly stained toroidal structure in FIG. 19A represents the myelin sheath of a single axon. (Bar=20 μm). Controls using preimmune serum did not show any detectable staining.

EXAMPLE 6

Mapping of the mouse PMP-22 gene to chromosome 11

Figure 9:
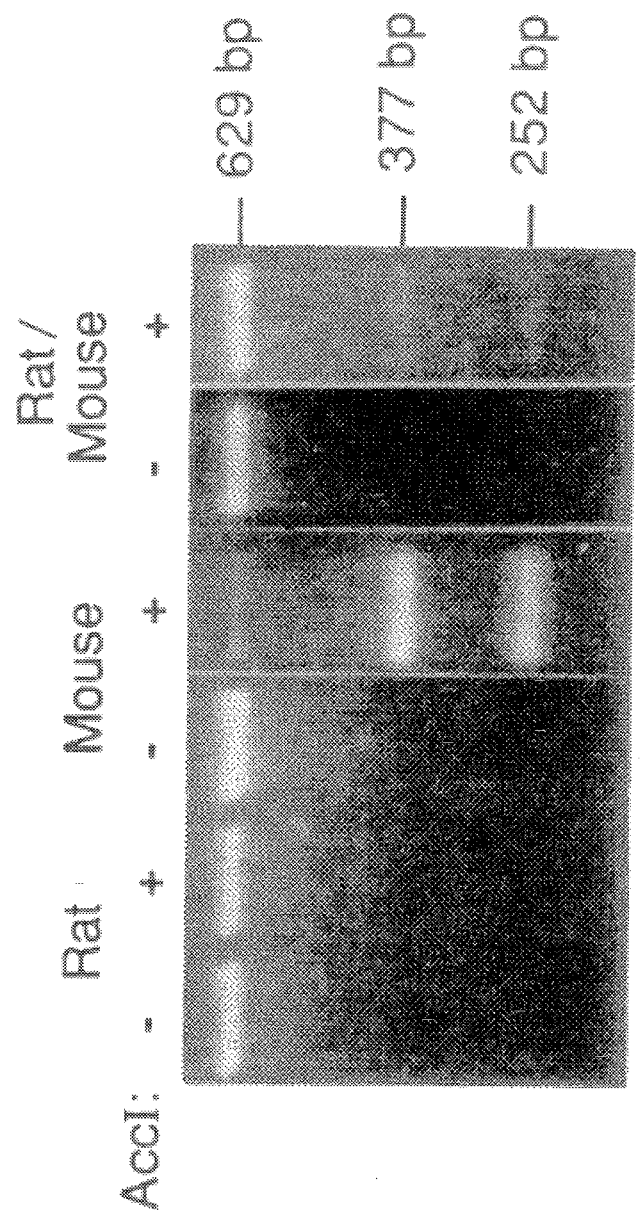
FIG. 9 shows PCR amplification products from genomic DNA isolated from a mapping panel of rat x mouse hybrid cell RTM9 (RAT/MOUSE) line analyzed by PCR using two oligonucleotide primers from rat PMP-22 cDNA.

DNA isolated from a mapping panel of hybrid cell lines was analyzed by PCR (Mullis; Mullis, et al.) using two oligonucleotide primers spanning nucleotides 873 to 889 and 1505 to 1489 of the rat PMP-22 cDNA (56; FIG. 16A), identical to positions 919 to 935 and 1547 to 1531 (except for nucleotide 1537) in the corrected mouse gas3 CDNA (57; FIG. 13). The results of this analysis are shown in FIG. 9. In the figure, genomic mouse (labelled MOUSE) and rat DNA (labelled RAT) were used as controls in parallel amplifications and AccI-analyses. Amplification products from the mouse×rat hybrid RTM9 are marked RAT/MOUSE.

EXAMPLE 7

Transverse Sections of Sciatic Nerves from +/+ and Tr/+ 23-day-old Litter-mate Mice Immediately after cervical dislocation, the segment of sciatic nerve in the thigh was dissected out and frozen for RNA extraction. Then the segment of sciatic nerve between the iliac crest and the vertebral column was excised and immersed in 4% paraformaldehyde and 2% glutaraldehyde in 0.1 M phosphate buffer, Ph 7.4 at 4° C. The tissue was washed in the same buffer containing 3% sucrase, and then post-fixed in 1% osmium tetroxide in the buffer-sucrose medium for two hours at 4° C. The tissue was dehydrated in graded ethanols and embedded in "EPON." The 1 μm sections were stained with alkaline toluidine blue. The results are shown in FIG. 10A and 10B. In the figure, the +/+ nerve (FIG. 10A) shows densely stained compact myelin sheaths encircling unstained axons of various calibers. The myelin sheath thicknesses are essentially proportional to the calibre of the individual axons they enclose. The Tr/+ nerve (FIG. 10B) shows relatively few well myelinated axons, though the axons themselves are similar in calibre to those in the littermate control specimen. The majority of the axons have very thin or absent myelin sheaths, but are contacted by Schwann cells with prominent nuclei and, at times, voluminous cytoplasm. The concentration of nuclei is increased relative to the control, in keeping with previously reported data (51). The scale bar an each figure equals 16 μm.

EXAMPLE 8

Identification of the Putative Tr Allele

A. Identification

Figure 11:
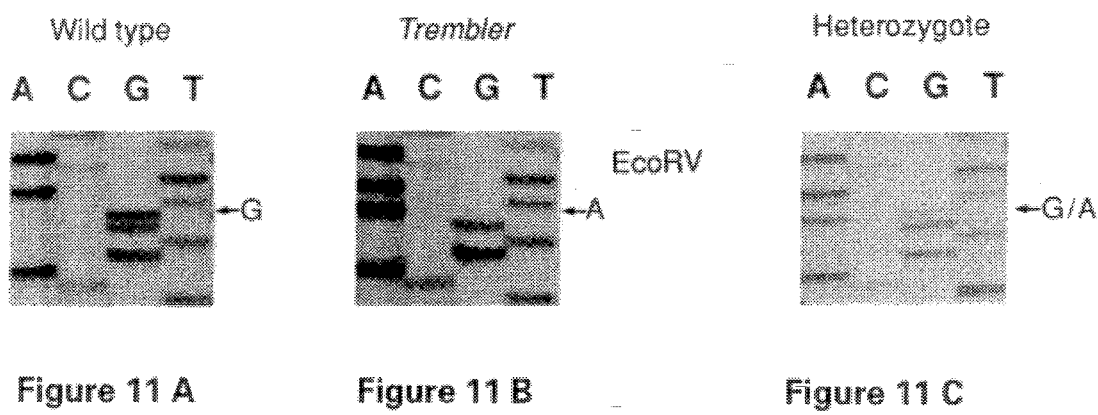
FIGS. 11A–11C shows identification of a Tr allele using dideoxynucleotide DNA sequencing of DNA obtained from PCR amplification of RNA isolated from sciatic nerves of wild type (FIG. 11A), trembler (FIG. 11B) and inbred heterozygous (FIG. 11C) mice.

Total RNA was isolated from the sciatic nerve of inbred, heterozygous Tr mice (a pair of siblings). The RNA was reverse-transcribed and PCR amplification was performed using two oligonucleotide primers spanning positions 91 to 109 and 832 to 814 in the corrected mouse gas3 sequence (57; FIG. 13). The PCR products were cloned using a "TA CLONING KIT" (Invitrogen) and the entire coding region of each of four independent clones was analyzed by dideoxynucleotide DNA sequencing. In FIG. 11B, a G to A transition mutation was found in two of the clones at position 635 (labelled *Trembler*). The sequences of the other two clones were wild type (labelled *Wild Type*; FIG. 11A). To rule out possible PCR errors and to visualize heterozygosity, independent PCR amplifications were performed and the products were directly sequenced (labelled *Heterozygote*; FIG. 11C) using a gas3-specific oligonucleotide primer (positions 521 to 537). The order of nucleotides on the sequencing gels is given at the top of the photographs of the gels. The respective nucleotides at the critical position 635 are marked with arrows. A novel EcoRV restriction endonuclease cleavage site, diagnostic for the putative Tr allele, is indicated.

B. Segregation of the putative Tr allele

Figure 12:
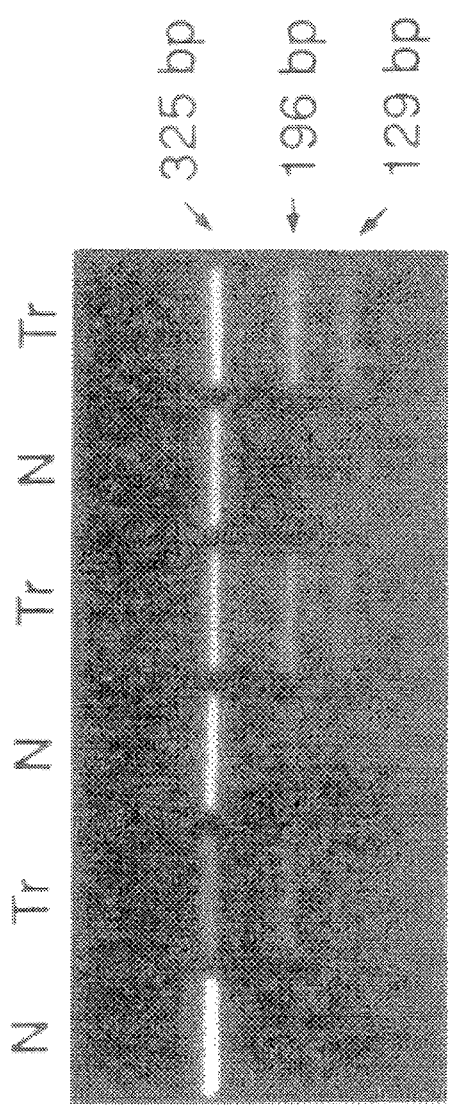
FIG. 12 shows segregation of a Tr allele from genomic DNA isolated from heterozygous Tr animals (Tr) and normal littermates (N)

Genomic DNA was isolated from three heterozygous Tr animals (labelled Tr; FIG. 12) and three normal littermates (labelled N; FIG. 12). PCR was carried out using two oligonucleotide primers spanning nucleotides 508 to 524 and 832 to 814, respectively (57; FIG. 13). The PCR products were cut with the restriction endonuclease EcoRV and analyzed on a 2% agarose gel. The 325 bp DNA fragment represents the wild type allele while fragments of 129 bp and 196 bp indicate the presence of the Tr allele (FIG. 12). The results were confirmed by direct sequencing of the PCR products as described above in Example 8A.

EXAMPLE 9

Corrected amino acid sequence of the mouse PMP-22 protein

The sequence determined above (FIG. 13) differs from the previously described amino-acid sequence of gas3 (57) in the 25 carboxy-terminal residues due to a CDNA sequencing error in the original report (a cytosine nucleotide is missing in the gas3 CDNA sequence at position 591; 57). The correct nucleotide at this position was initially identified by direct sequencing of PCR products obtained from reverse-transcribed total RNA isolated from growth-arrested NIH3T3 fibroblasts. The amino acid sequence is given in the one-letter code and the site of the putative Tr mutation is marked with an arrow. Putative membrane-associated domains of the PMP-22 protein are underlined.

Figure 14:
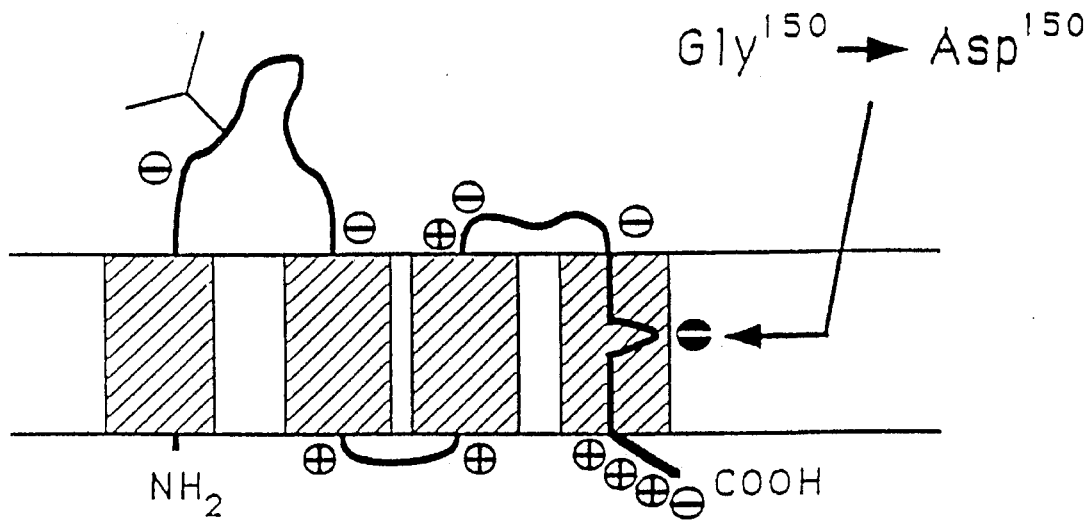
FIG. 14 shows a schematic model of PMP-22 protein structure, based on the primary sequence shown in FIG. 13, where putative membrane associated domains are underlined.

FIG. 14 presents a putative model of the PMP-22 protein structure. The positions of charged amino acids (neutral pH) are indicated as "+" or "−". The location of the putative Tr mutation is marked with an arrow. The model is based on computer-generated hydrophobicity plots, surface probability and secondary structure predictions (62).

EXAMPLE 10

Nucleotide Sequence of a Human PMP-22 cDNA and Predicted Amino Acid Sequence of the Human PMP-22 Protein A. The Nucleotide Sequence The human cDNA sequence was derived from overlapping clones isolated by screening of a human brain cDNA library (Stratagene) and using RT-PCR carried out with human dorsal root ganglia (DRG) RNA using oligonucleotides based on the rat PMP-22/SR13 nucleotide sequence (21; FIG. 16A).

In FIG. 1, plain numbers refer to the nucleotide sequence, while numbers next to arrows refer to the amino acid sequence. Putative membrane-spanning domains are underlined. The cDNA sequence shown represents a consensus sequence of partial cDNA sequences derived from the above-discussed overlapping clones isolated by screening of a human brain cDNA library.

The DNA sequence of the entire human PMP-22 cDNA coding region was confirmed by partial sequencing of the corresponding genomic PMP-22 gene (FIG. 5) as well as cDNA clones obtained by RT-PCR (DRG-derived RNA) using human specific PMP-22 oligonucleotides specific for the 5' and 3' untranslated regions.

B. Comparison of the PMP-22 Amino Acid Sequences of Human, Rat, Mouse and Bovine FIG. 2 presents a comparison of PMP-22 amino acid sequences. The human, rat and mouse amino acid sequences are derived from cloned cDNA sequences (14,21; and data presented above), while the partial bovine sequence represents direct amino acid sequencing from two regions of the PASII protein (19,21). In FIG. 2, amino acid residues which differ from the human sequence are indicated. Identical amino acids are represented by hyphens. 'X' in the bovine sequence identifies an undetermined amino-acid residue. 'TM' refers to putative transmembrane domains.

EXAMPLE 11

Mapping of the PMP-22 Gene to the Human 17p11.2 - 17p12 region

Genomic DNA from a human control individual, a mouse TK- cell line, Ci-iD, the hamster HPRT cell line RJK88 and several somatic cell hybrids retaining portions of human chromosome 17 were digested with HindIII and the Southern blot hybridized to the cDNA probe phPMP22-1 as described previously (44). The results of the southern analysis are presented in FIG. 3.

In the figure hybrid lanes are identified by schematic idiograms representing portions of chromosome 17 retained in the hybrids. Lane 1, 5 ug of human DNA; lanes 2 and 3, 10 ug of Cl-1D (mouse) and RJK88 (hamster) DNA respectively; lanes 4–8, 10 ug of DNA from hybrids MH22-6, Hy254-1, Hy357-2D, LS-1 and 88H5, respectively. The migration of the molecular weight markers is shown on the right. Note the retention of the human PMP-22 genomic HindIII fragments of 7.4 kb and 2.5 kb only in lanes 4, 5 and 8 but not in lanes 6 and 7.

EXAMPLE 12

Expression Pattern of PMP-22 in Human Tissues

A. Northern Analysis of Human RNAs with a PMP-22 cDNA probe

Approximately 5 ug of total RNA from human brain, spinal cord, femoral nerve, skeletal muscle, heart, liver, and lymphoblasts was subjected to northern hybridization as described above (Materials and Methods). The results of the northern analysis are presented in FIG. 4A.

The blot shown in FIG. 4A was stripped and probed with the cDNA for the ubiquitously expressed glyceraldehyde-3-phosphate dehydrogenase gene (G3PDH) as a control for the integrity and amounts of RNA in each lane. The results of this northern analysis are presented in FIG. 4B.

B. RT-PCR analysis of human RNAs using primers specific for the PMP-22 cDNA

Approximately 0.5 ug of total RNA from human brain spinal cord, femoral nerve, skeletal muscle, heart liver and lymphoblasts was used for RT-PCR amplification as described in above (Materials and Methods).

20 µl out of 50 µl of the reaction products were electrophoresed on a 2% agarose gel (FIG. 4C). The expected RT-PCR product of 470 bp was detected using femoral nerve and spinal cord RNA as template.

RT-PCR analysis was performed as just described, using primers specific for the G3PDH cDNA. The results of this analysis are presented in FIG. 4D. The expected RT-PCR product of 983 bp was noted in all tissues examined.

EXAMPLE 13

Genomic Clones for the PMY 22 Region

A cosmid contig was constructed for the PMP-22 genomic region by identification of overlapping cosmids from a cosmid library constructed from chromosome 17. In FIG. 5, fragments showing hybridization to the cDNA are indicated by bold lines. The thin vertical lines represent EcoRI sites and the asterisks indicate the position of the T3 polymerase promoter sequence in the vector. The names of the cosmids and subclones are indicated to the right of the line diagrams.

The numbers below the uppermost line refer to EcoRI fragment sizes in kb. The dotted lines represent regions where the EcoRI restriction map is not available. The centromere-telomere orientations are based on the genetic map of chromosome 17 (45).

EXAMPLE 14

Figure 6:
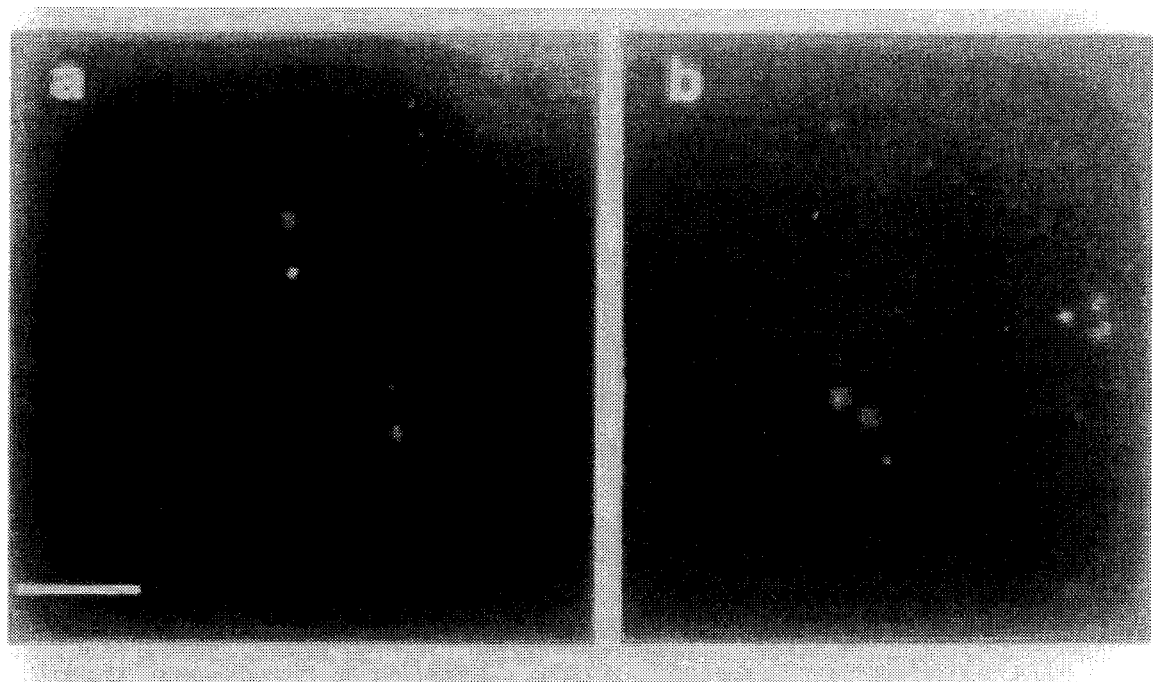
FIGS. 6A and 6B show fluorescence in situ hybridization (FISH) of PMP-22 gene in control (FIG. 6A) and in CMT1A (FIG. 6B) individuals, where nuclei were hybridized simultaneously with biotinylated cosmid c132-G8 and digoxigenin-labeled cosmid c1516 (REF 46) which maps to human 17p11.2.

Fluorescence in situ Hybridization Analysis of the PMP-22 Gene in Control and CMT1A Individuals Interphase nuclei were prepared from lymphoblastoid lines of a control individual, HOU76-289 (3) (FIG. 6A) and from a CMT1A patient, HOU42-333 who is homozygous for the duplication mutation (44) (FIG. 6B). Nuclei were hybridized simultaneously with biotinylated cosmid c132-G8 representing a portion of the hpmp gene and digoxigenin-labeled cosmid c1516, which maps to 17p11.2, as described previously (46).

The hybridization sites of c132-G8 and c1516 were labeled with Texas red and fluorescein (Pierce), respectively, and viewed together through a double band-pass filter. The hybridization pattern of c1516 was used as an internal assay for the replication status of the proximal 17p region. The nucleus in FIG. 6B was counterstained with propidium iodide. The Bar in the lower left corner corresponds to approximately 5 µm.

EXAMPLE 15

Mendelian Inheritance of Dosage Differences of Polymorphic Alleles at the hpmp Locus in a CMT1A Nuclear Family Five µg of genomic DNA from individuals within a nuclear family (HOU42) of CMT1A patients (44) was digested with the enzymes HincII and EcoRI and Southern analysis (Maniatis, et al.; Ausubel, et al.) performed with the probe p132-G8R1. The results of the southern analysis are shown in FIG. 7B, after preassociation of repeats (44). The polymorphic site is a HincII site.

The members of the nuclear family are indicated above the autoradiograph (FIG. 7A). The individual genotypes are indicated below the pedigree, with the slash separating the pair of alleles segregating with CMT1A in the family. Note the difference in the relative intensity of alleles A and B in CMT1A patients 218, 220, 222, 223, and 224 versus unaffected individuals 219, 289, 221, 290 and 291.

EXAMPLE 16

Pulsed Field Analysis of Control and CMT1A Individuals Maps the hpmp Gene Within the CMT1A Duplication Region Pulsed field analysis was performed as described previously (3) on genomic DNA from lymphocytes of control and CMT1A individuals with the probe p103-B11RH4 (FIG. 8A) and with the probe p132C38-RA7 (FIG. 8B).

p103-B11RH4 is a 3.7 kb EcoRI/HindIII fragment containing the third exon of the hpmp gene which was subcloned from within the 8.2 kb EcoRI fragment of c103-Ell and p132G8-RAT is a 2.2 kb EcoRI/AscI fragment from cosmid c132-GB (see FIG. 5).

In FIGS. 8A and 8B—Lane 1, control male SD; lanes 2, 4, 6, 8, 10, control male MM; lanes 3, 5, 7, 9, 11, CMT1A patient HOU1-3. CMT1A-specific duplication junction fragments were identified by the enzymes SacII, FspI and AscI when hybridized with the probe in panel B, but not that in panel A.

FIG. 8C shows the pulsed Geld map of the hpmp and VAW409 region deduced from the above-described hybridizations. In FIG. 8C, A AscI; F, FspI; N, NotI; S, SacII; Sf SfiI. Centromere-telomere orientation is based on the genetic map of chromosome 17 (45). The boxed AscI, FspI and SacII sites are those introduced by the duplication event in CMT1A patients and hence, the map on the centromeric side of these novel sites is different in CMT1A patients. The SacII site marked with an asterisk is polymorphic; FIG. 8B shows that it is absent in individual SD (lane 1) but present in individuals MM (lane 2) and 1–3 (lane 3).

While the invention has been described with reference to specific methods and embodiments, it will be appreciated that various modifications and changes may be made without departing from the invention.

---

It is claimed:

1. A purified nucleic acid sequence having the sequence SEQ ID NO: 1, said sequence encoding a peripheral myelin protein characterized by (i) expression predominantly by peripheral Schwann cells, (ii) a molecular weight of about 20,000, and (iii) substantial sequence homology to a peripheral myelin protein obtained from human peripheral nervous tissue.

* * * * *